(12) United States Patent
Bender, II

(10) Patent No.: US 11,759,599 B2
(45) Date of Patent: Sep. 19, 2023

(54) SYSTEMS AND METHOD FOR VALVE CONTROL IN A FILL ASSEMBLY OF A MEDICAL DEVICE

(71) Applicant: GE Precision Healthcare LLC, Milwaukee, WI (US)

(72) Inventor: Thomas Lane Bender, II, Cottage Grove, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 490 days.

(21) Appl. No.: 16/914,173

(22) Filed: Jun. 26, 2020

(65) Prior Publication Data
US 2021/0402131 A1 Dec. 30, 2021

(51) Int. Cl.
| | |
|---|---|
| *A61M 16/18* | (2006.01) |
| *B67D 7/36* | (2010.01) |
| *A61M 39/22* | (2006.01) |
| *B67C 3/26* | (2006.01) |
| *B67D 3/00* | (2006.01) |
| *B67C 3/28* | (2006.01) |

(52) U.S. Cl.
CPC .......... *A61M 16/183* (2013.01); *A61M 39/22* (2013.01); *B67C 3/2637* (2013.01); *B67D 3/0003* (2013.01); *B67D 3/0083* (2013.01); *B67D 7/367* (2013.01); *A61M 2039/226* (2013.01); *A61M 2209/045* (2013.01); *B67C 3/28* (2013.01); *B67C 3/285* (2013.01); *B67D 3/0025* (2013.01)

(58) Field of Classification Search
CPC ............ A61M 39/22; A61M 2039/226; A61M 2209/045; B67C 3/2637; B67C 3/28; B67D 3/0025
See application file for complete search history.

(56) References Cited

U.S. PATENT DOCUMENTS

| | | | | |
|---|---|---|---|---|
| 6,138,672 A | * | 10/2000 | Kankkunen | A61M 16/183 141/2 |
| 6,817,390 B2 | * | 11/2004 | Falligant | A61M 16/183 128/202.22 |
| 6,929,041 B2 | * | 8/2005 | Falligant | A61M 16/183 141/351 |
| 8,033,306 B2 | * | 10/2011 | Freed | A61M 16/183 141/351 |
| 8,528,550 B2 | * | 9/2013 | Cuzyldo | A61M 16/183 222/546 |

(Continued)

FOREIGN PATENT DOCUMENTS

| | | |
|---|---|---|
| WO | 2008151667 A1 | 12/2008 |
| WO | 2010109488 A1 | 9/2010 |

(Continued)

*Primary Examiner* — Nicolas A Arnett

(57) ABSTRACT

Systems and methods are provided for a valve shut-off system of a medical device. In one embodiment, the valve shut-off system of the medical device includes a first pin movable between a first position where a valve is opened and a second position where the valve is closed, the first pin including a slot, and a second pin having a mating geometry with the slot of the first pin, the second pin adjustable between a locked position that holds the first pin in the first position and an unlocked position that enables movement of the first pin between the first position and the second position.

8 Claims, 16 Drawing Sheets

(56) References Cited

U.S. PATENT DOCUMENTS

| | | | | |
|---|---|---|---|---|
| 8,552,839 B2* | 10/2013 | Archer | ............... | H04W 60/00 |
| | | | | 235/385 |
| 9,186,478 B2* | 11/2015 | Schnaars | ............ | A61M 16/183 |
| 10,758,647 B2* | 9/2020 | Tobien | ..................... | F16K 3/24 |
| 11,324,913 B2* | 5/2022 | Bender, II | ........... | A61M 16/183 |
| 2008/0236576 A1* | 10/2008 | Falligant | ............ | A61M 16/183 |
| | | | | 128/203.12 |
| 2010/0000958 A1* | 1/2010 | Mitchell | ............ | A61M 16/183 |
| | | | | 215/40 |
| 2010/0211019 A1* | 8/2010 | Greco | .............. | A61M 5/16881 |
| | | | | 604/246 |
| 2013/0126464 A1* | 5/2013 | Manzke | .................... | B65B 3/04 |
| | | | | 141/2 |
| 2015/0217080 A1* | 8/2015 | Manzke | ............. | A61M 16/183 |
| | | | | 141/2 |
| 2015/0306339 A1* | 10/2015 | Danielsen | ......... | A61M 16/0051 |
| | | | | 128/203.14 |
| 2015/0320116 A1* | 11/2015 | Bleloch | ............... | A61M 11/042 |
| | | | | 219/628 |
| 2016/0361514 A1* | 12/2016 | Warby | ............... | A61M 16/104 |
| 2017/0182281 A1* | 6/2017 | Kersey | .................. | A61M 16/18 |
| 2017/0259026 A1* | 9/2017 | Mair | ........................ | B65B 3/04 |

FOREIGN PATENT DOCUMENTS

| | | | |
|---|---|---|---|
| WO | 2010147843 | A1 | 12/2010 |
| WO | 2016059038 | A1 | 4/2016 |

* cited by examiner

SYSTEMS AND METHOD FOR VALVE CONTROL IN A FILL ASSEMBLY OF A MEDICAL DEVICE

FIELD

Embodiments of the subject matter disclosed herein relate to systems and methods for a fill assembly of a medical device.

BACKGROUND

Some types of medical equipment, such as anesthetic vaporizers, may include a reservoir or sump for storing a liquid medical agent (such as anesthetic agent, saline, etc.). The reservoir may be refillable by attaching a refill bottle to a fill assembly of the reservoir, for example. In some examples, the fill assembly of the reservoir and the refill bottle may each include a spring-biased valve that can be pushed open to enable the liquid medical agent to flow from the refill bottle to the fill assembly. Further, each valve may be shut to seal the correspond vessel (e.g., the reservoir or the refill bottle). For example, when a neck of the refill bottle is inserted into the fill assembly, the neck of the refill bottle may push open the valve of the fill assembly, and a component of the fill assembly may push open the valve of the refill bottle. Thus, the insertion and removal of the neck of the refill bottle in the fill assembly may control the opening and closing of the valves, and thus control medical agent flow from the refill bottle to the fill assembly.

BRIEF DESCRIPTION

This summary introduces concepts that are described in more detail in the detailed description. It should not be used to identify essential features of the claimed subject matter, nor to limit the scope of the claimed subject matter.

In one aspect, a valve shut-off system for a medical device can include a first pin movable between a first position where a valve is opened and a second position where the valve is closed, the first pin including a slot, and a second pin having a mating geometry with the slot of the first pin, the second pin adjustable between a locked position that holds the first pin in the first position and an unlocked position that enables movement of the first pin between the first position and the second position. In this way, the second pin may be adjusted between the locked position and the unlocked position in order to control opening of the valve.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Embodiments of the present disclosure will now be described, by way of example, with reference to the FIGS. 1A-11, which relate to various embodiments for a valve shut-off system that may be used to control fluid communication between a reservoir of a medical device and a refill bottle, for example. The valve-shut-off system may be the valve shut-off system schematically shown in FIGS. 1A-1D or the valve shut-off system schematically shown in FIG. 2, for example. The valve shut-off system may include a fill assembly of the reservoir, such as the example fill assembly shown in FIGS. 3A-3C, that includes an overfill prevention apparatus. The overfill prevention apparatus may include a slide pin, such as the slide pin shown in FIGS. 4A and 4B, that includes a mating slot and a rotating pin, such as the rotating pin shown in FIGS. 5A and 5B, that is positioned within the mating slot and includes a mating geometry with the mating slot. The rotating pin may be adjusted within the mating slot between a locked position and an unlocked position, such as shown in FIGS. 6A and 6B, respectively. In the locked position, the rotating pin may hold the slide pin in an extended position with respect to the reservoir, and while in the locked position, the slide pin may open a valve of the refill bottle (e.g., a refill bottle valve) to enable a medical agent to flow from the refill bottle to the reservoir. In the unlocked position, the rotating pin may not hold the slide pin in the extended position, and the slide pin may move to a retracted position with respect to the reservoir. In the retracted position, the slide pin may not engage with the refill bottle valve, may not make contact with the refill bottle valve, or may have minimal contact with the refill bottle valve. As a result, the slide pin may not open the refill bottle valve while in the retracted position, and the medical agent may not flow from the refill bottle to the reservoir.

Figure 8A:
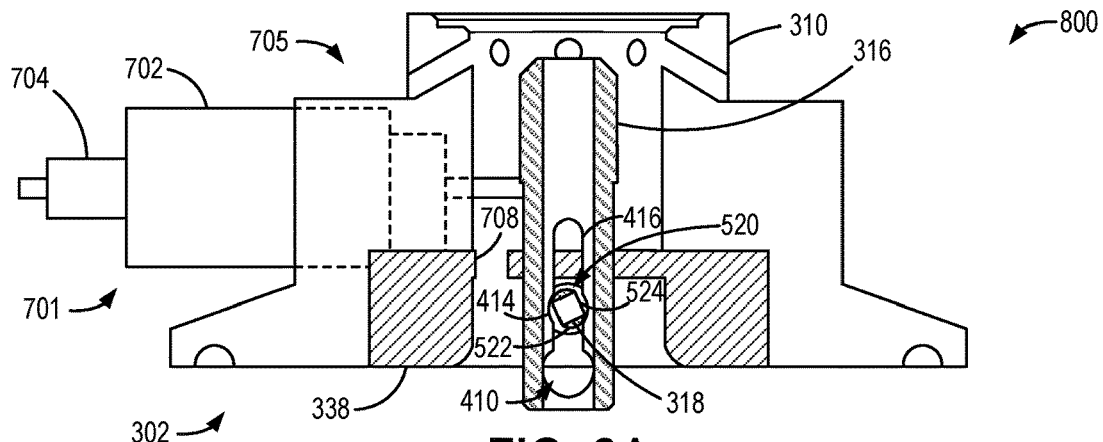
FIGS. 8A-8C depict cross-sectional views demonstrating actuation of the electro-mechanical actuator of FIGS. 7A-7B, according to an embodiment.
Figure 8B:
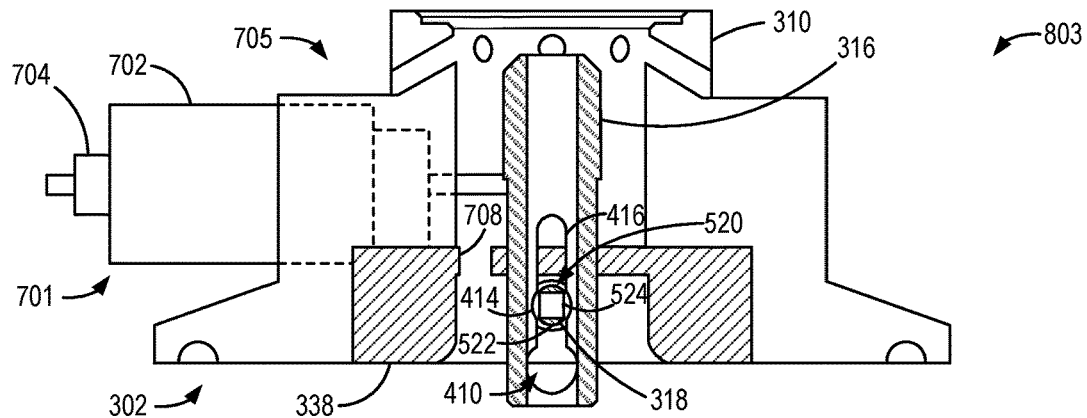
Figure 8C:
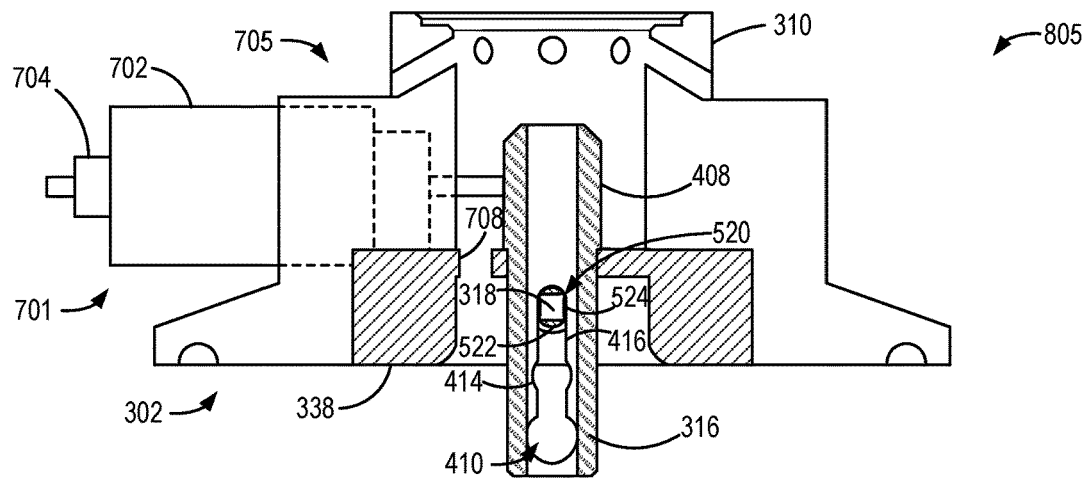
Figure 9A:
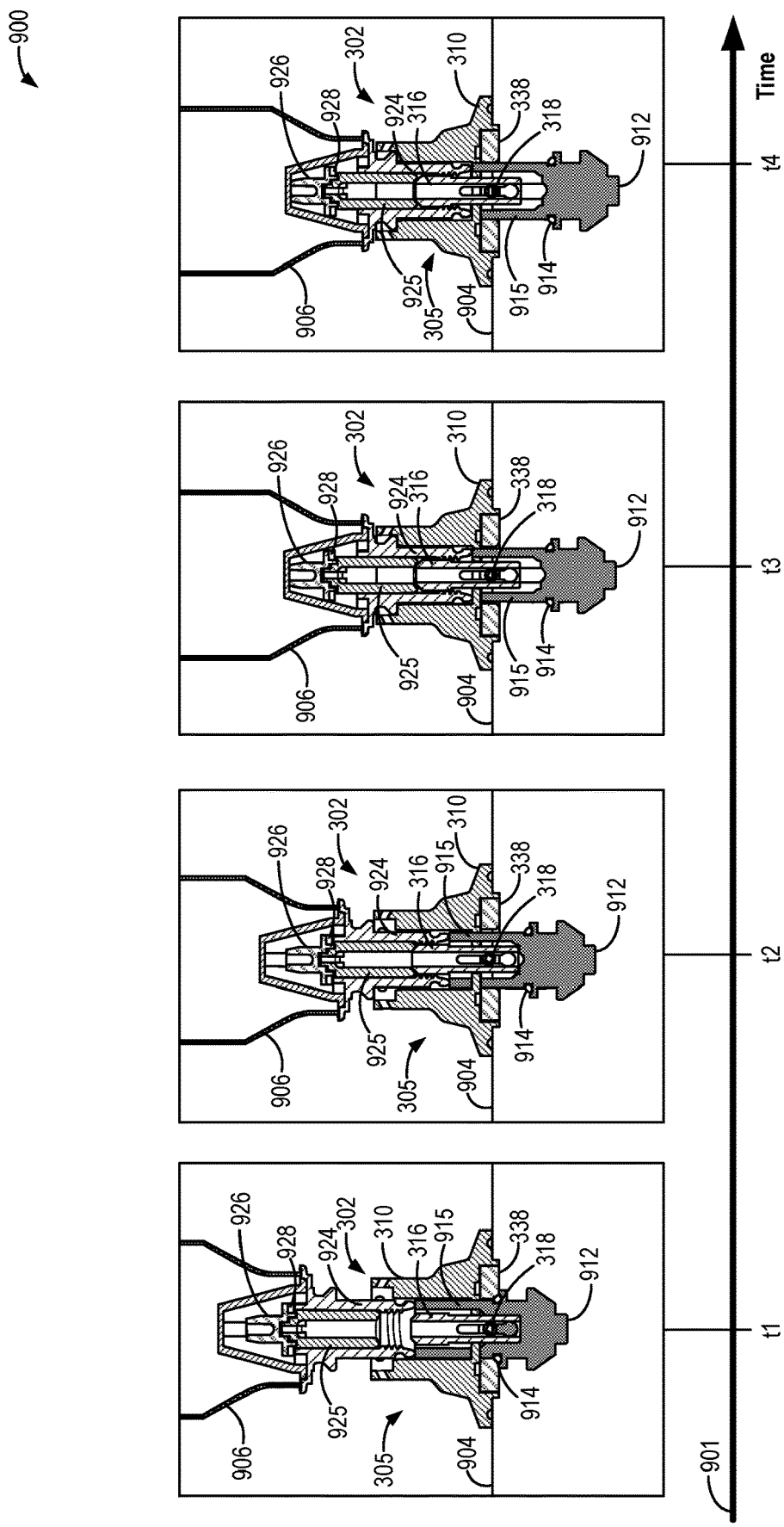
FIGS. 9A and 9B schematically show a sequence of operating a valve shut-off system to enable and disable flow between a refill bottle and a reservoir, according to an embodiment.
Figure 9B:
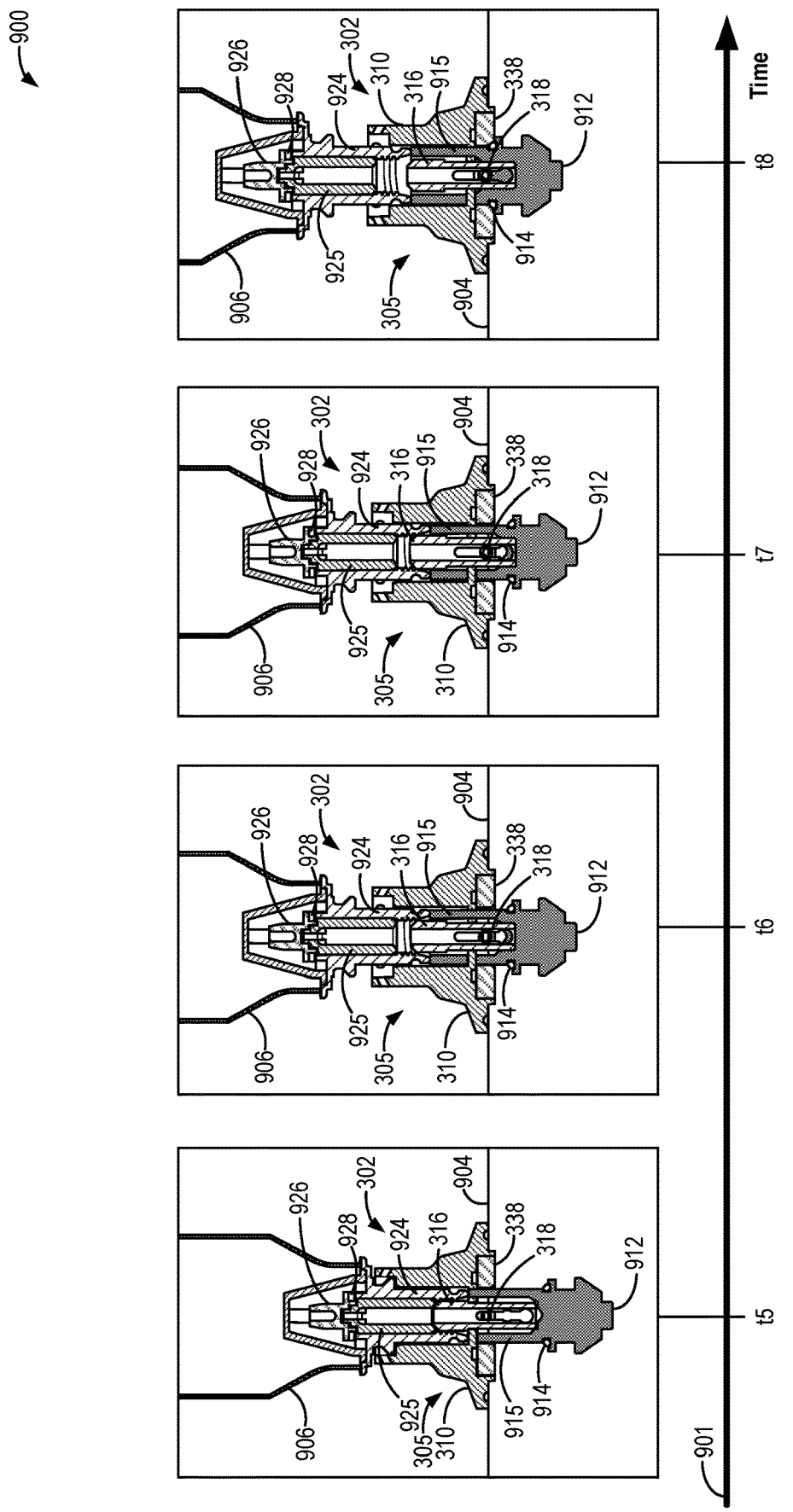

The rotating pin may be adjusted between the locked position and the unlocked position via an actuator. In some embodiments, the actuator may be an electro-mechanical actuator, such as in the embodiment shown in FIGS. 7A and 7B. FIGS. 8A-8C demonstrate actuation of the electro-mechanical actuator of FIGS. 7A and 7B to adjust the rotating pin between the locked and unlocked positions. Further, FIGS. 9A and 9B schematically show a sequence of operating the valve shut-off system to enable and disable flow between the refill bottle and the reservoir, such as according to a high-level example method shown in FIG. 10. In particular, via the valve shut-off system, a valve of the reservoir (e.g., a reservoir valve) is opened before the refill bottle valve when the refill bottle is inserted into the fill assembly of the reservoir, and the refill bottle valve closes before the reservoir valve when the refill bottle is removed from the fill assembly. FIG. 11 shows a flow chart of a method for controlling an electro-mechanical actuator, such as the electro-mechanical actuator of FIGS. 7A and 7B, to adjust the rotating pin between the locked and unlocked positions, thereby controlling fluid communication between the refill bottle and the reservoir. By controlling the fluid communication between the refill bottle and the reservoir via the overfill prevention apparatus in the valve shut-off system, overfilling of the reservoir may be reduced or avoided.

Advantages that may be realized in the practice of some embodiments of the described systems and techniques are that medical agent waste and user exposure to the medical agent may be reduced. For example, by preventing or reducing overfilling of the reservoir, the medical agent may not spill out of the reservoir. Overfilling occurs when the refill bottle that is attached to the reservoir via the fill assembly still contains medical agent when the reservoir reaches its "full" capacity and cannot accept additional medical agent. Further, an inherent geometry of a nozzle (or neck) of the refill bottle nozzle may trap liquid medical agent and/or medical agent vapors between the refill bottle and the reservoir, whether the reservoir is overfilled or not. In contrast, the embodiments described herein enable the refill bottle valve and the reservoir valve to open and close at different timings, and no longer synchronized, which allows the medical agent to drain into the reservoir immediately after the bottle valve closes. For example, the overfill prevention apparatus of the fill assembly controls the communication of the medical agent to the reservoir instead of an insertion state of the refill bottle controlling opening and closing of both the refill bottle and the reservoir valve. As such, the refill bottle may remain attached to the reservoir without risking overfilling and without relying on a user to track medical agent transfer between the refill bottle and the reservoir or a fill level of the reservoir.

Once a pre-determined amount of time has elapsed or a desired amount of the medical agent has entered the reservoir, for example, the overfill prevention apparatus automatically disengages the refill bottle valve, which stops the flow of the medical agent from the refill bottle to the reservoir. The reservoir valve remains open, allowing for gravity-assisted draining of residual medical agent in the fill assembly. As a result, medical agent is not trapped between the refill bottle valve and the reservoir valve, further reducing medical agent waste and user exposure to the medical agent. When the refill bottle is removed from the fill assembly, the reservoir valve closes.

As a further example, by automatically disengaging (e.g., fully closing) the refill bottle valve after the pre-determined amount of time has elapsed or the desired amount of medical agent has entered the reservoir, a minimum desired head space volume may be maintained within the reservoir above a liquid level of the medical agent. For example, when the medical agent is volatile, the minimum desired head space volume may prevent the reservoir from becoming overly pressurized. Overall, the valve shut-off system described herein enables a volume of the medical agent in the reservoir to be optimized while reducing user exposure to the medical agent and environmental accumulation of the medical agent. Further, by automatically stopping communication between the refill bottle and the reservoir via the overfill prevention apparatus, a demand on the user may be decreased, enabling the user to focus on other tasks and increasing user satisfaction.

Figure 1A:
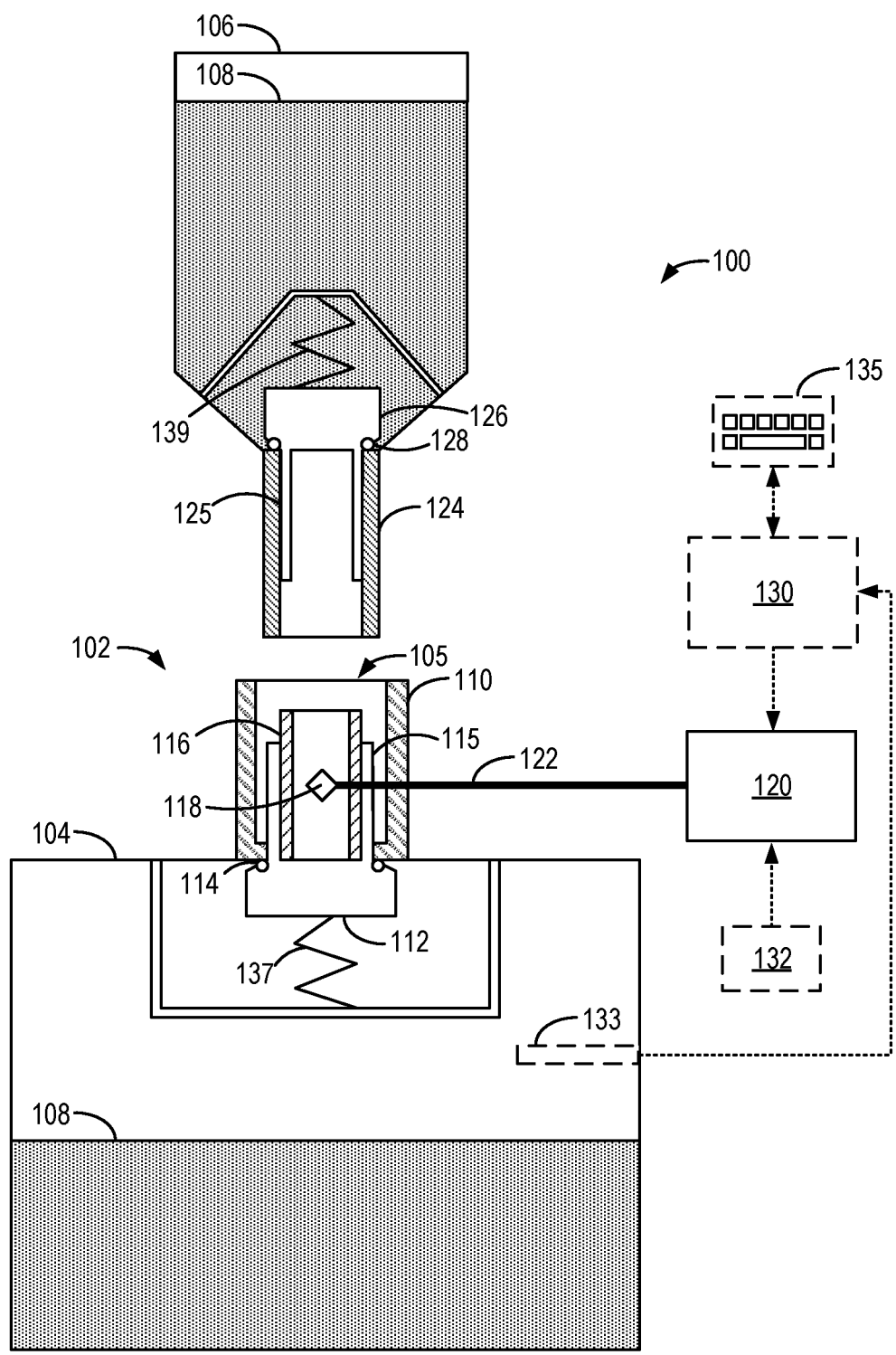
FIGS. 1A-1D schematically show a valve shut-off system, according to an embodiment.
Figure 1B:
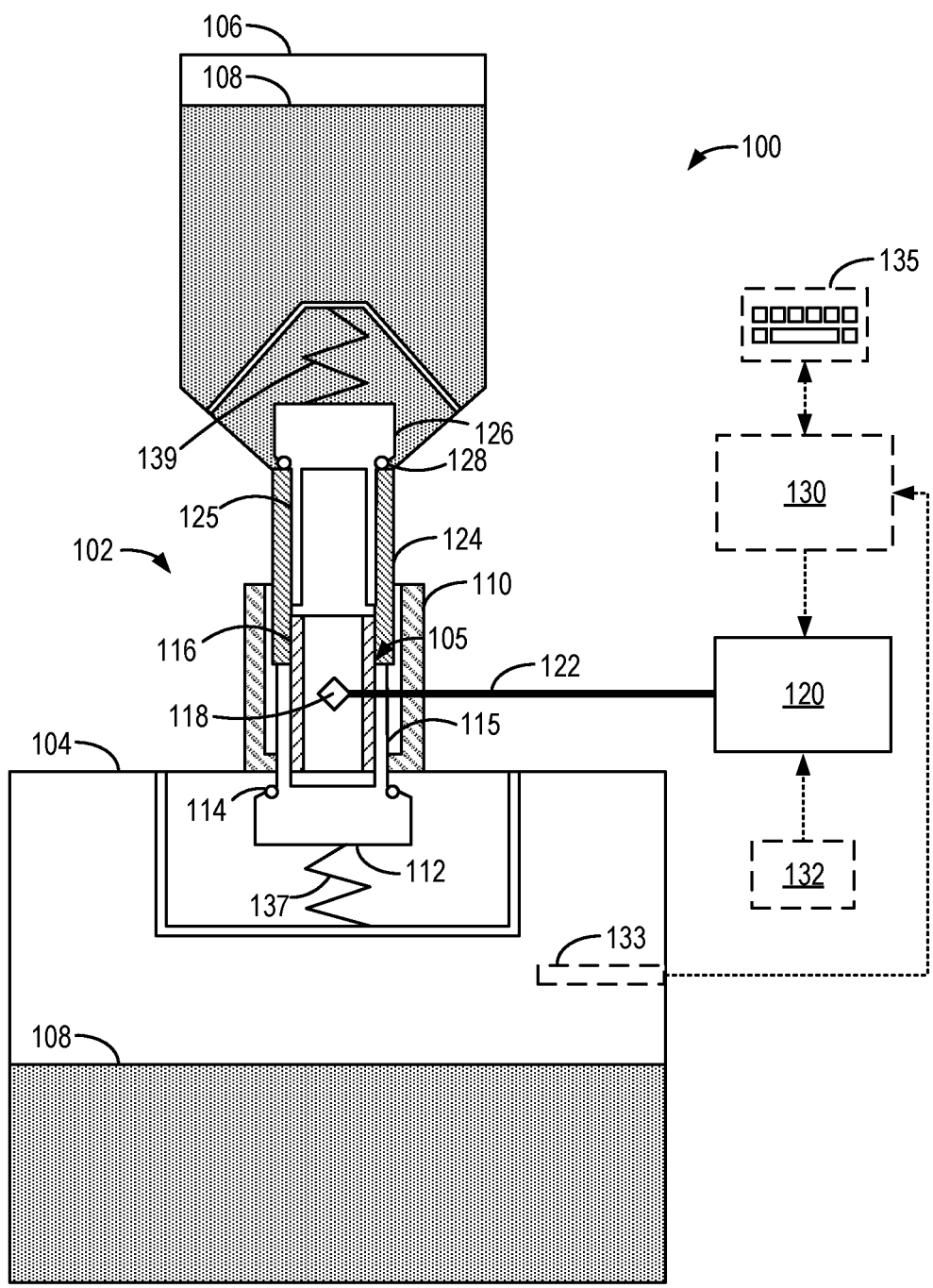
Figure 1C:
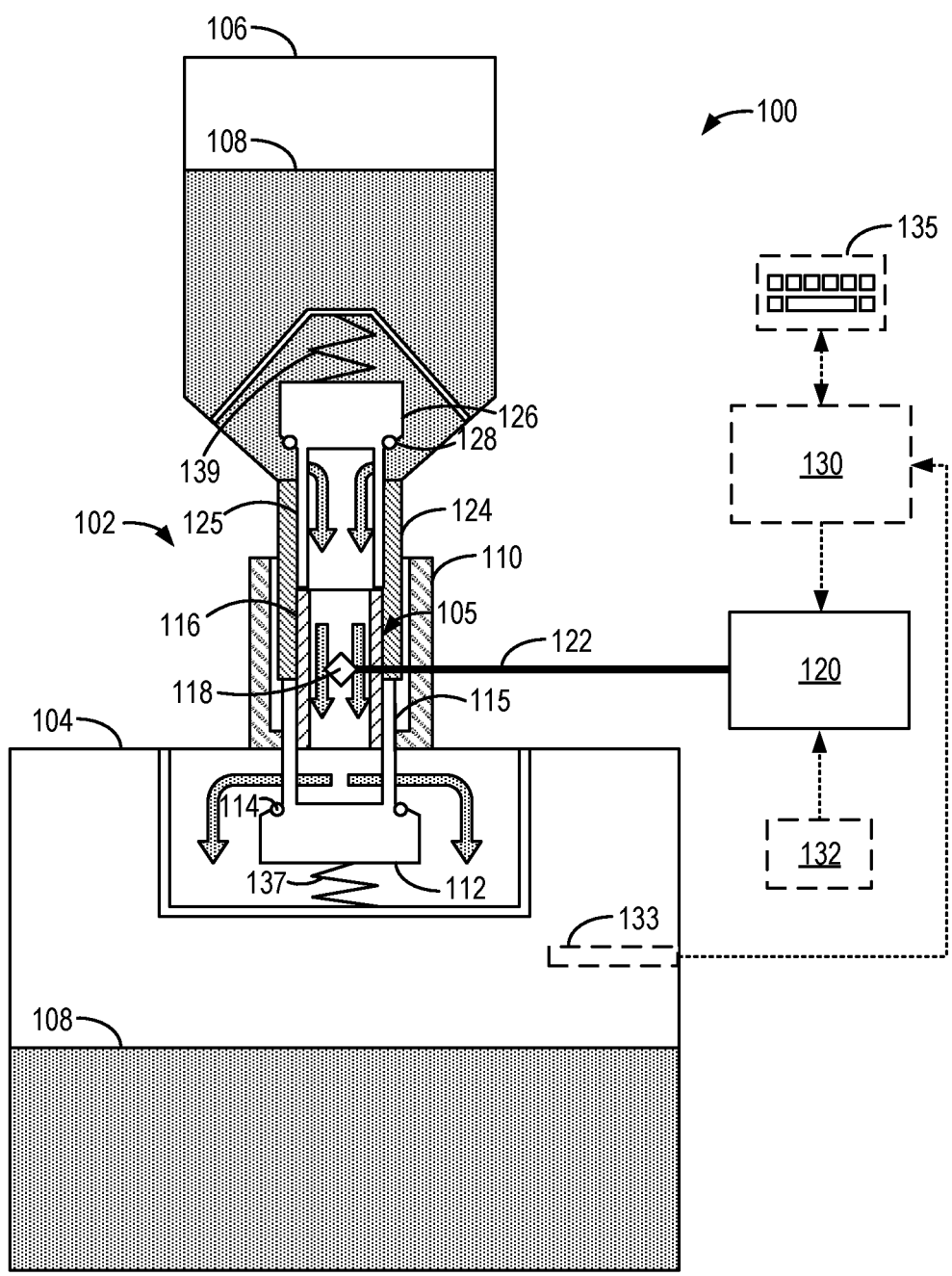
Figure 1D:
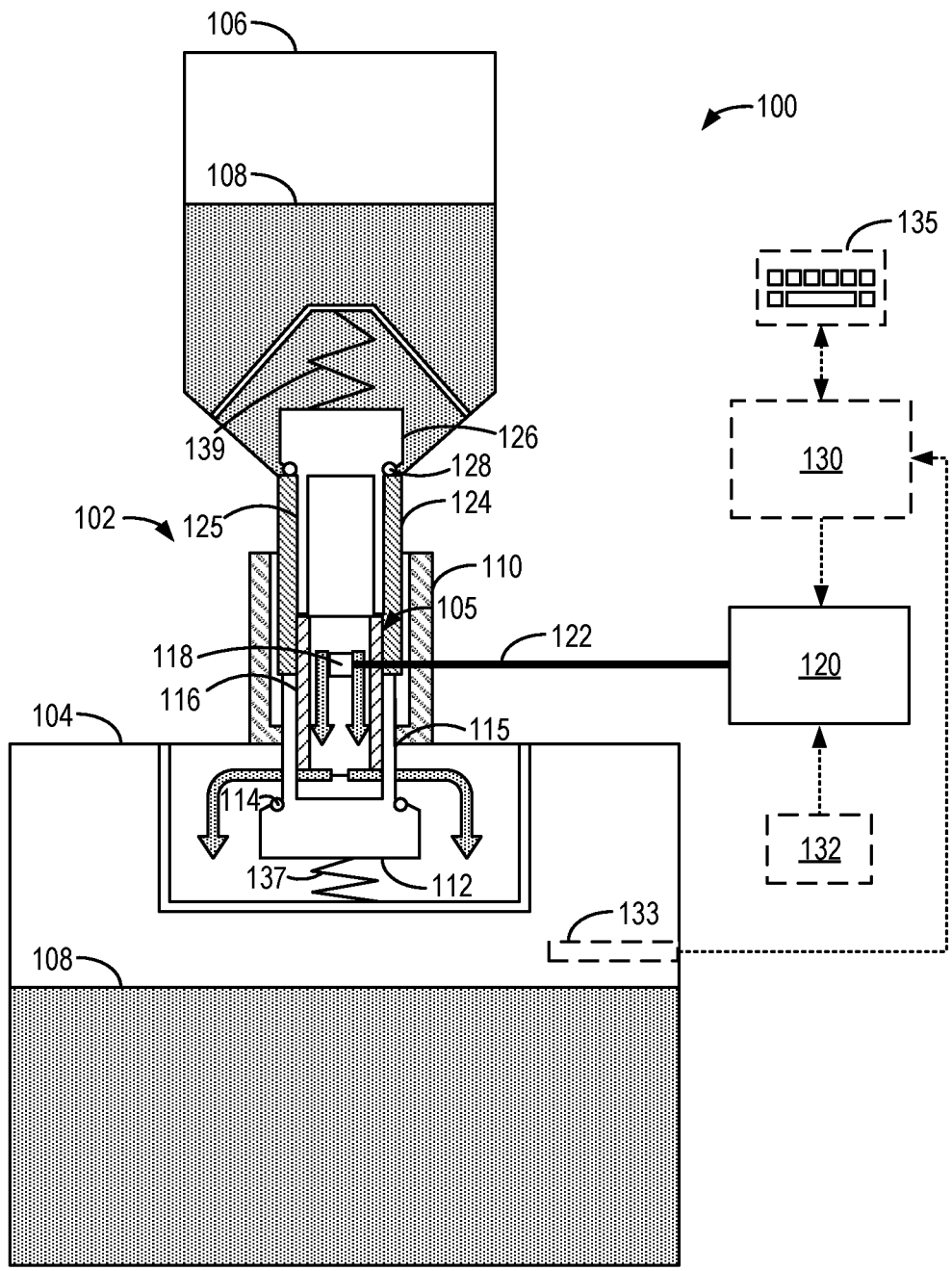

Turning now to the figures, FIGS. 1A-1D schematically show an embodiment of a valve shut-off system 100 that may be included in a medical device. The valve shut-off system 100 may be at least partially included in a fill assembly 102 of a medical device reservoir 104. The medical device reservoir 104 may be a sump, for example, or another receptacle configured to hold (or store) a medical agent 108. The medical agent 108 may be any liquid or semifluid medical agent, such as an anesthetic agent, saline, sterile water, or a liquid medicine, for example. The fill assembly 102 is shaped to receive a refill bottle 106, and the refill bottle 106 is also configured to hold/store the medical agent 108. FIG. 1A shows the refill bottle 106 prior to insertion in the fill assembly 102, FIG. 1B shows the refill bottle 106 inserted into the fill assembly 102 by a first amount, with the refill bottle 106 engaging and opening the fill assembly 102 (as will be elaborated below), FIG. 1C shows the refill bottle 106 inserted into the fill assembly 102 by a second, greater amount, with flow enabled from the refill bottle 106 to the medical device reservoir 104, and FIG. 1D shows the refill bottle inserted into the fill assembly 102 by the second amount and with flow disabled from the refill bottle 106 to the medical device reservoir 104.

The fill assembly 102 includes a fill neck 110 positioned on an external surface of the medical device reservoir 104 and a fill assembly valve 112 (e.g., a valve of the medical device reservoir 104) that extends from an interior of the medical device reservoir 104 to a central cavity of the fill neck 110. In particular, the fill assembly valve 112 includes a fill assembly valve seal 114 positioned within the interior of the medical device reservoir 104 and a fill assembly valve stem 115 that extends from the interior of the medical device reservoir 104 to the central cavity of the fill neck 110. The fill assembly valve 112 further includes a bias spring 137 that applies a spring force to the fill assembly valve 112 in a first direction. When a force applied to the fill assembly valve 112 in a second direction, opposite the first direction, is less than the spring force of the bias spring 137, the fill assembly valve 112 is held in a closed position shown in FIG. 1A. In the closed (e.g., fully closed) position, the fill assembly valve seal 114 is in direct contact with a bottom surface of the fill neck 110, forming a liquid- and gas-tight seal between the fill neck 110 and the interior of the medical device reservoir 104 and blocking fluid (e.g., gas and liquid) flow into the medical device reservoir 104.

Similarly, the refill bottle 106 includes a refill bottle neck 124 positioned on an external surface of the refill bottle 106 and a refill bottle valve 126 that extends from an interior of the refill bottle 106 to a central cavity of the refill bottle neck 124. In particular, the refill bottle valve 126 includes a refill bottle valve seal 128 positioned within the interior of the refill bottle 106 and a refill bottle valve feature 125 that extends from the interior of the refill bottle 106 to the central cavity of the refill bottle neck 124. As an example, the refill bottle valve feature 125 may be a valve neck or stem. The refill bottle neck 124 is shaped for insertion within the central cavity of the fill neck 110 and to engage with the fill assembly valve stem 115, as will be elaborated herein. The refill bottle valve 126 further includes a bias spring 139 that applies a spring force to the refill bottle valve 126 in a third direction, which may be the second direction described above in some examples. When a force applied to the refill bottle valve 126 in a fourth direction, opposite the third direction, is less than the spring force of the bias spring 139, the refill bottle valve 126 is held in a closed (e.g., fully closed) position shown in FIG. 1A. In the closed position, the refill bottle valve seal 128 is in direct contact with a surface of the refill bottle neck 124, forming a fluid-tight seal between the refill bottle neck 124 and the interior of refill bottle 106 and blocking fluid (e.g., gas and liquid) flow between the refill bottle 106 and the central cavity of the refill bottle neck 124.

The fill assembly 102 further includes an overfill prevention mechanism (or apparatus) 105 including a first pin 116 and a second pin 118. As will be elaborated herein, the first pin 116 is selectively positioned to engage with the refill bottle valve feature 125. For example, the first pin 116 is moveable between a first, extended position (e.g., extended further from the medical device reservoir 104) that engages with the refill bottle valve feature 125 and a second, retracted position (e.g., retracted further into the medical device reservoir 104) that does not engage with the refill bottle valve feature 125 in order to prevent fluid coupling between the refill bottle 106 and the medical device reservoir 104. The first pin 116 may be a substantially hollow cylindrical tube, and the second pin 118 may be peg-like or rod-like, for example. In another example, the first pin 116 may be a solid pin that pushes on flat face. The position of the first pin 116 is at least partially controlled by a position of the second pin 118, which may be adjusted via an actuator 120. For example, the second pin 118 may be adjustable between a first, locked position and a second, unlocked position via movement of the actuator 120. The movement of the actuator 120 may be transferred to the second pin 118 via a mechanical linkage 122 to move the second pin 118 between the locked position and the unlocked position. When the second pin 118 is in the locked position, the first pin 116 is held in the extended position and may thus engage with the refill bottle valve feature 125. When the second pin 118 is in the unlocked position, the first pin is moveable between the extended position and the retracted position.

The second pin 118 may hold the first pin 116 in the extended position by preventing movement of the first pin 116 between the extended position and the retracted position. For example, the second pin 118 may mate with or otherwise engage with a hole or slot in the first pin 116, as will be elaborated herein. In one embodiment, adjusting the second pin 118 between the locked position and the unlocked position may include extending and retracting the second pin 118 with respect to the first pin 116. For example, the second pin 118 may be inserted into the hole or slot in the first pin 116 when in the locked position and not when the second pin 118 is in the unlocked position. In another embodiment, the second pin 118 is rotated between the locked position, which mates with the hole or slot in the first pin 116, and the unlocked position, which does not mate with the hole or slot in the first pin 116, without extending or retracting the second pin 118 relative to the first pin 116. Thus, the locked position may be a first rotated position, and the unlocked position may be a second rotated position having a different rotational angle than the first rotated position.

The actuator 120 may be a mechanical or an electro-mechanical actuator. Further, although the actuator 120 is schematically shown external to the medical device reservoir 104, in some embodiments, the actuator 120 is internal to the medical device reservoir 104, as will be elaborated below with particular reference to FIG. 2. For example, the actuator 120 may be a float that rises or falls depending on a level (e.g., height or volume) of the medical agent 108 within the medical device reservoir 104. As another example, the actuator 120 may be a mechanical timer (e.g., a mechanical spring timer) that triggers the second pin 118 to move from the locked position to the unlocked position upon elapsing. As still another example, the actuator 120 may be a manual push button that triggers the second pin 118 to move from the locked position to the unlocked position when pushed by a user.

In embodiments where the actuator 120 is an electro-mechanical actuator, the valve shut-off system 100 optionally includes a controller 130 and a power source 132 electronically coupled to the actuator 120. The power source 132 may be a battery, a super capacitor, or a mains supply at a wall outlet, for example. The controller 130 may communicate with the actuator 120 to adjust the second pin 118 between the locked position and the unlocked position. As will be elaborated herein with particular respect to FIGS. 7A-8C and FIG. 11, the actuator 120 may be a solenoid, and the controller 130 may adjust an energization state of the solenoid, such as from an energized state to a de-energized state or vice versa, to adjust the second pin 118 from the locked position to the unlocked position.

In some embodiments, the valve shut-off system 100 further includes a medical agent level circuit including a level sensor 133, shown optionally in FIGS. 1A-1D. In such embodiments, the controller may adjust the actuator 120, and thus the position of the second pin 118, based on the level of the medical agent 108 within the medical device reservoir 104, as indicated by the level sensor 133. The level sensor 133 may be any type of analog or digital level sensor, such as an infrared level sensor, a float-type level sensor, a capacitive level sensor, an inductive level sensor, an ultrasound-based level sensor, a time-of-flight level sensor, or a level switch (e.g., a Hall effect level switch).

Further still, in some embodiments, the valve shut-off system 100 further includes a user interface 135. In some electro-mechanical embodiments, the user interface 135 may be in electronic communication with the controller 130. The user interface 135 may be configured to both output information to the user (e.g., via a display screen and/or speakers) and receive inputs from the user (e.g., via a touchscreen, a touchpad, a stylus, a mouse, and/or a keyboard). In this way, the user may communicate with the controller 130 to request a refill event of the medical device reservoir 104, to manually trigger actuation of the actuator 120, etc. In other embodiments (e.g., both mechanical and some electro-mechanical), the user interface 135 may be a mechanical-type user interface that includes an additional mechanical input to the mechanical linkage 122.

Referring to FIG. 1B, the refill bottle 106 is shown partially inserted into the fill assembly 102. In particular, the refill bottle neck 124 is engaged with the fill assembly valve stem 115, pushing the fill assembly valve 112 in the second direction with a force that overcomes the spring force of the bias spring 137. As a result, the fill assembly valve seal 114 no longer in direct contact with the fill neck 110, and the fill assembly valve 112 is opened. The second pin 118 is in the locked position, holding the first pin 116 in the extended position. However, the first pin 116 is not engaged with the refill bottle valve feature 125. Thus, the geometries of the fill assembly valve stem 115, the refill bottle neck 124, the first pin 116, and the refill bottle valve feature 125 are such that during insertion, the refill bottle neck 124 engages with the fill assembly valve stem 115 before the first pin 116 engages with the refill bottle valve feature 125. For example, the fill assembly valve 112 is opened when the refill bottle neck 124 is inserted into the fill neck 110 by at least a first distance, while the refill bottle valve 126 is not opened when the refill bottle neck 124 is inserted into the fill neck 110 by the first distance. As one non-limiting example, the first distance is within a range between 10 and 13 millimeters, such as approximately 12 millimeters.

Referring next to FIG. 1C, the refill bottle 106 is shown further inserted into the fill assembly 102 than in FIG. 1B (e.g., inserted a greater distance into the fill assembly 102 than in FIG. 1B). The fill assembly valve 112 is opened to a greater degree in FIG. 1C than in FIG. 1B, as the further insertion of the refill bottle neck 124 presses the fill assembly valve 112 into the interior of the medical device reservoir 104 by a greater distance. Further, the second pin 118 remains in the locked position, holding the first pin 116 in the extended position. The first pin 116 engages with the refill bottle valve feature 125, pushing the refill bottle valve 126 in the fourth direction and overcoming the spring force of the bias spring 139. The refill bottle valve seal 128 is no longer in direct contact with the refill bottle neck 124, and the refill bottle valve 126 is open. For example, the refill bottle valve 126 is opened when the refill bottle neck 124 is inserted into the fill neck 110 by at least a second distance, greater than the first distance, and when the first pin 116 is locked in the extended position by the second pin 118. As one non-limiting example, the second distance is within a range between 13 and 16 millimeters, such as approximately 14 millimeters. As a result, the medical agent 108 flows from an interior of the refill bottle 106, through the open refill bottle valve 126 and the refill bottle neck 124, through the substantially hollow first pin 116, and into the interior of the medical device reservoir 104 via the open fill assembly valve 112, as indicated by shaded arrows.

Although FIG. 1D shows the refill bottle 106 inserted into the fill assembly 102 by a same amount as FIG. 1C, the second pin 118 is in the unlocked position. For example, the second pin 118 is adjusted from the locked position shown in FIG. 1C to the unlocked position shown in FIG. 1D by the actuator 120 responsive to a mechanical trigger (such as the mechanical timer elapsing, the user depressing the manual push button, the float reaching the threshold level, etc.) or electrical trigger (e.g., received from the controller 130, the user interface 135, and/or the level sensor 133). As a result of the second pin 118 being in the unlocked position, the first pin 116 is no longer held in the extended position. The spring force of the bias spring 139 no longer experiences resistance from the first pin 116 because the second pin 118 has been moved to the unlocked position, allowing the first pin 116 to be pushed away from the extended position to the retracted position by the force of the bias spring 139. Because the first pin 116 no longer engages with the refill bottle valve feature 125, the force of the bias spring 139 also closes and seals the refill bottle valve 126. Thus, the medical agent 108 no longer flows from the interior of the refill bottle 106 to the refill bottle neck 124. Further, the refill bottle valve feature 125 pushes the first pin 116 into the retracted position as the refill bottle valve 126 is closed.

However, because the refill bottle 106 is still inserted into the fill neck 110 by a distance greater than the first distance, the fill assembly valve 112 remains open, and remaining medical agent 108 within the refill bottle neck 124 and the fill assembly 102 (e.g., within the first pin 116) may flow into the medical device reservoir 104, as shown by the shaded arrows. The fill assembly valve 112 may close as the refill bottle 106 is withdrawn from the fill neck 110, becoming fully closed when the refill bottle neck 124 is inserted into the fill neck 110 by less than the first distance described above. As the fill assembly valve 112 closes, the fill assembly valve 112, through bias spring 137, pushes the first pin 116 back to the extended position as the refill bottle 106 is removed. For example, a surface of the fill assembly valve 112 may come into contact with a bottom surface of the first pin 116 to push the first pin 116 back to the extended position. With the first pin 116 in the extended position, the second pin 118 may reset (e.g., engage/lock or remain disengaged/unlocked from the first pin 116) depending on the level of the medical agent 108 in the medical device reservoir 104.

Thus, actuating the second pin 118 to the unlocked position enables the bias spring 139 of the refill bottle valve 126 to force the first pin 116 into the retracted position, which is partially within the medical device reservoir 104, and close the refill bottle valve 126. Further, actuating the second pin 118 to the unlocked position does not affect the position of the fill assembly valve 112. By closing the refill bottle valve 126 prior to closing the fill assembly valve 112 via the valve shut-off system 100, the medical agent 108 may be more completely delivered to the medical device reservoir 104, and trapped medical agent 108 within the fill assembly 102 may be reduced or eliminated.

Figure 2:
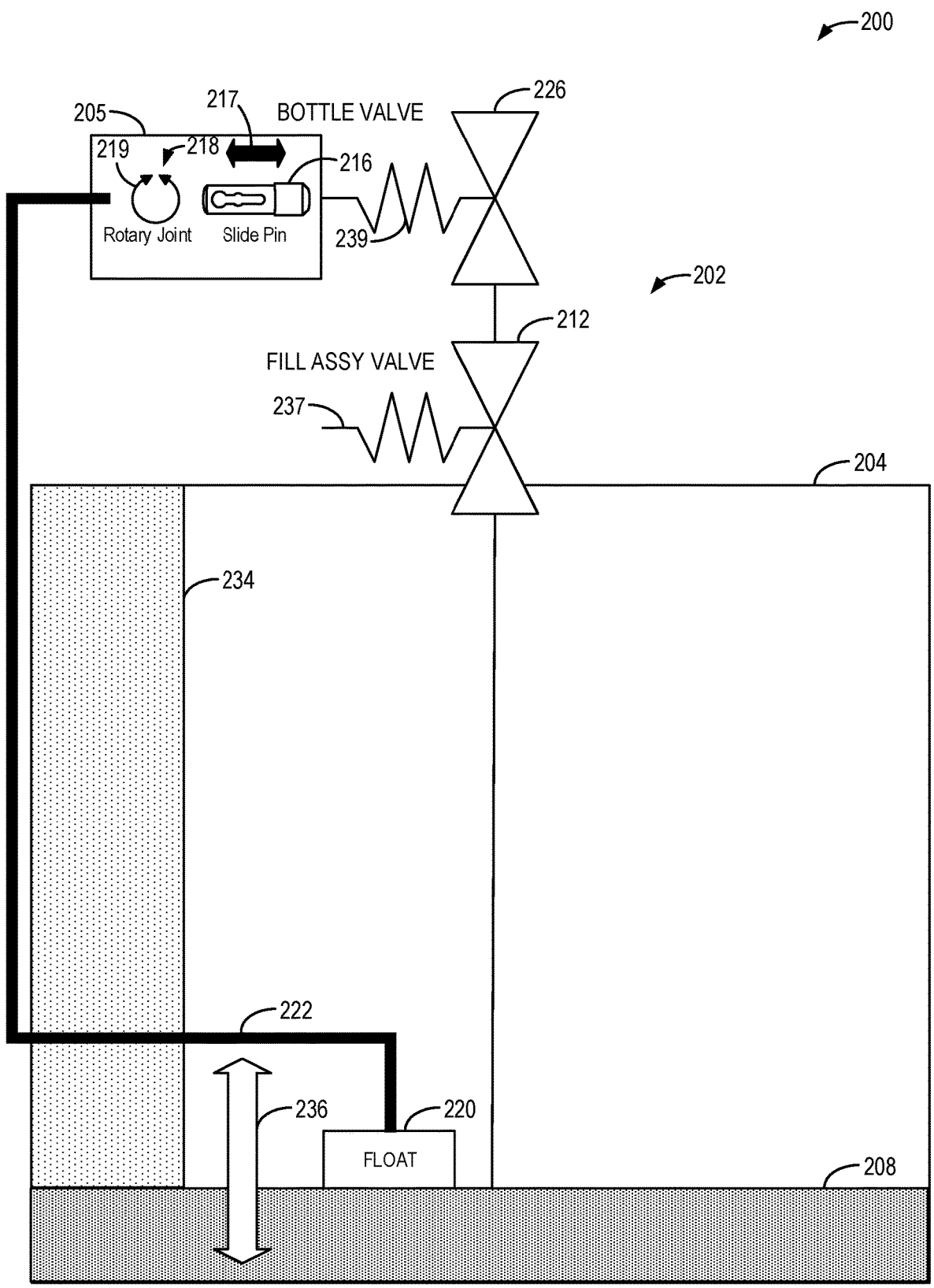
FIG. 2 shows a schematic valve diagram of a valve shut-off system including a mechanical actuator, according to an embodiment.

Next, FIG. 2 schematically shows a valve diagram of a valve shut-off system 200 including a mechanical actuator. The valve shut-off system 200 may be one embodiment of the valve shut-off system 100 of FIGS. 1A-1D, for example. Thus, components of FIG. 2 that correspond to components introduced in FIGS. 1A-1D are numbered similarly (e.g., 202 of FIG. 2 corresponds to 102 of FIGS. 1A-1D) and function as previously described. Further, some components introduced in FIGS. 1A-1D are omitted from the schematic shown in FIG. 2 to highlight functional linkages between components.

FIG. 2 shows a fill assembly valve 212 of a medical device reservoir 204 holding a medical agent 208. The fill assembly valve 212, included in a fill assembly 202, is a mechanically actuated valve having a bias spring 237 that holds the fill assembly valve 212 closed when a force applied on the fill assembly valve 212 in the opposite direction of the bias spring 237 is less than a spring force applied by the bias spring 237, as described above with respect to FIGS. 1A-1D. FIG. 2 also shows a refill bottle valve 226, which is a mechanically actuated valve including a bias spring 239 that holds the refill bottle valve 226 closed when a force applied on the refill bottle valve 226 in the opposite direction of the bias spring 239 is less than a spring force applied by the bias spring 239.

The medical device reservoir 204 includes a buoyant float 220 positioned therein that is mechanically coupled to an overfill prevention mechanism 205 via a mechanical linkage 222. The float 220 sits substantially on top of the medical agent 208, tracking with a level of the medical agent 208 within a range of movement 236. For example, the float 220 may not fall below a lower bound of the range of movement 236 or rise above an upper bound of the range of movement 236. A head volume 234 of the medical device reservoir 204 may hold vapors of the medical agent 208 and/or air, for example. The upper bound of the range of movement 236 may be calibrated to maintain the head volume 234 at no less than a calibrated minimum volume for desired storage properties. For example, when the medical agent 208 is volatile, the head volume 234 may keep the medical device reservoir 204 from becoming pressurized. The head volume 234 may be a function of liquid medical agent 208 volume expansion due to storage temperature and residual agent remaining between the refill bottle valve 226 and the fill assembly valve 212, for example. The more liquid medical agent 208 that exists, the more head volume 234 is needed for agent expansion. Further, the shape of the medical device reservoir 204 may also influence a volumetric calculation of the minimum volume for the head volume 234, as a tall and skinny reservoir may need more head "distance" than short and wide reservoir. As one non-limiting example, the minimum volume for the head volume 234 may be approximately 10% of a total capacity of the medical device reservoir 204. As an illustrative example, the minimum volume for the head volume 234 may be 35 milliliters (mL) when the total capacity of the medical device reservoir 204 is 350 mL. Thus, in this example, between 0 and 315 mL of the medical agent 208 may be stored in the medical device reservoir 204.

As a position of the float 220 changes within the range of movement 236, the mechanical linkage 222 adjusts a position of a rotating pin 218 (e.g., the second pin 118 of FIGS. 1A-1D) directly mechanically coupled to the mechanical linkage 222 and having a rotary joint 219 with a slide pin 216 (e.g., the first pin 116 of FIGS. 1A-1D) of the overfill prevention mechanism 205. For example, as a volume of the medical agent 208 increases, the buoyancy force increases on the float 220. Once a threshold buoyancy force is achieved, the rotating pin 218 rotates within the rotary joint 219, releasing the slide pin 216 and allowing it to retract from its extended position. The threshold buoyancy force may correspond to a force for overcoming friction of the rotary joint 219 to rotate the rotating pin 218.

The slide pin 216 has a range of movement 217 between a first position (e.g., the extended position of FIGS. 1A-1D) that engages with the refill bottle valve 226 and a second position (e.g., the retracted position of FIGS. 1A-1D) that does not engage with the refill bottle valve 226. The position of the slide pin 216 depends at least partially on a rotational angle (Ø) of the rotating pin 218 within the rotary joint 219, which depends on the position of the float 220 (Y1) within the range of movement 236. The position of the refill bottle valve 226 in turn depends at least partially on the position of the slide pin 216 (Y2) within the range of movement 217. The position of the fill assembly valve 212 depends on a distance of insertion (D) of a neck of the refill bottle (e.g., refill bottle neck 124 of FIGS. 1A-1D) into a fill neck of the medical device reservoir 204 (e.g., fill neck 110 of FIGS. 1A-1D).

For example, as will be illustrated in FIG. 9A, the fill assembly valve 212 may be opened when D is between a first threshold insertion distance and a maximum insertion distance (11.7 mm<D<19.2 mm in one non-limiting, illustrative example). The maximum insertion distance may be defined by a physical geometry of the fill neck, for example. The refill bottle valve 226 may be opened when D is between a second threshold insertion distance, greater than the first threshold insertion distance, and the maximum insertion distance (14.4 mm<D<19.2 mm in one non-limiting, illustrative example), but only when Y2 is between a minimum extended distance and a maximum extended distance (0.1 mm<Y2<5.9 mm in one non-limiting, illustrative example). When Y2 is less than the minimum extended distance (e.g., Y2=0 mm), the refill bottle valve 226 may not open, even when D is between the second threshold insertion distance and the maximum insertion distance. Further, Y2 may be between the minimum extended distance and the maximum extended distance only when Y1 is between a lower threshold agent level and an upper threshold agent level (0 mm<Y1<10 mm in one non-limiting, illustrative example). The upper threshold agent level may correspond to the minimum volume for the head volume 234. Additionally or alternatively, the upper threshold agent level may correspond to a level at which the buoyancy force of the float 220 overcomes the friction force of the rotary joint 219. The friction force is a function of the spring force of bias spring 239, a design of the overfill prevention mechanism 205, and materials of the slide pin 216 and the rotating pin 218 (e.g., for ease of movement). Once the buoyancy force (which is a function of the volume of the medical agent 208 and a density of the medical agent 208) overcomes the friction force, linear or rotational movement of the mechanical linkage 222 begins due to movement of the float 222 (Y1). Thus, the movement of the mechanical linkage 222 is a function of the volume of the medical agent 208, the density of the medical agent 208, and Y1. The movement of the mechanical linkage 222 is translated into movement of the rotating pin 218 at the rotary joint 219, resulting in slide pin 316 changing its state from being locked in its extended position to being released to its retracted position (e.g., Y2<0.1 mm). Thus, when Y1 is not less than the upper threshold agent level (e.g., Y1=10 mm), Y2 is brought to below the minimum extended distance, and the refill bottle valve 226 is not opened.

The rotating pin 218 may hold the slide pin 216 in the first position (e.g., where Y1 is between the minimum extended distance and the maximum extended distance) when Ø is less than a threshold rotational angle (e.g., 0°<Ø<45°). For example, the rotating pin 218 is held in the locked position within the slide pin 216, described above with respect to FIGS. 1A-1D, when Ø is less than the threshold rotational angle. The rotating pin 218 may transition to the unlocked position when Ø is not less than the threshold rotational angle (e.g., Ø is greater than or equal to the threshold rotational angle). Further, the rotational angle of the rotating pin 218 within the rotary joint 219 is less than the threshold rotational angle while Y1 is less than the threshold agent level. Thus, responsive to Y1 reaching the threshold agent level, the mechanical linkage 222 rotates the rotating pin 218 such that Ø meets or exceeds threshold rotational angle, and the rotating pin 218 is transitioned from the locked position to the unlocked position. Responsive to the rotating pin 218 transitioning to the unlocked position, the slide pin 216 is no longer held in the extended position, and the spring force of the bias spring 239 forces the slide pin 216 into the retracted position, where Y2 is less than the minimum extended distance, and closes the refill bottle valve 226.

By triggering closing of the refill bottle valve 226 when the position of the float 220 reaches the threshold agent level via the overfill prevention mechanism 205, overfilling of the medical device reservoir 204 may be prevented or avoided. As a result, adequate head volume 234 may be maintained within the medical device reservoir 204. Further, the embodiment shown in FIG. 2 is fully mechanical, with the level of the medical agent 208 within the medical device reservoir 204 controlling the overfill prevention mechanism 205. Thus, the valve shut-off system 200 may enable or disable fluid communication between the refill bottle and the medical device reservoir 204 automatically and without manual user input or electronic control. Further, the valve shut-off system 200 may not use electrical power, enabling the valve shut-off system 200 to function without connection to a power source.

Figure 3A:
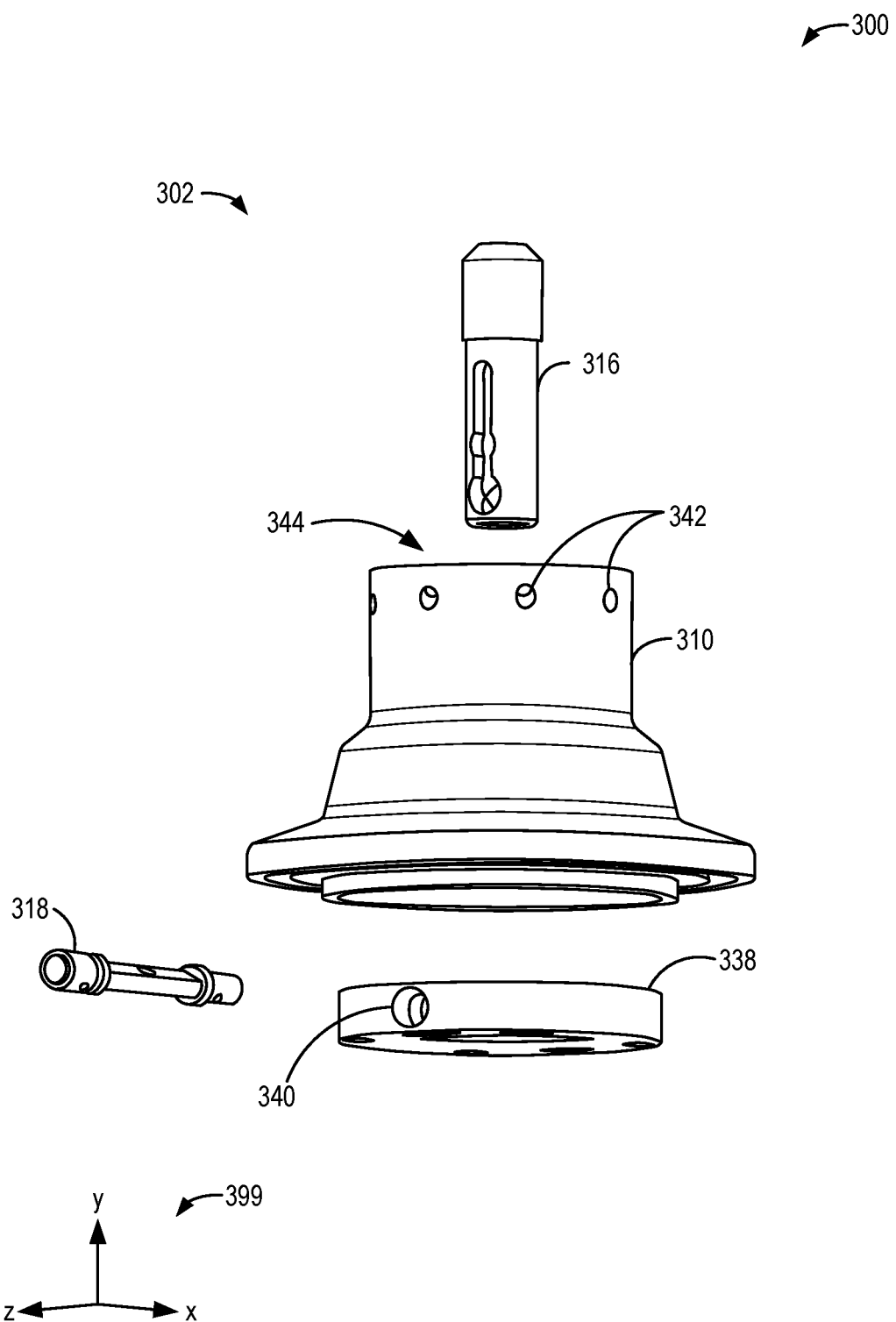
FIGS. 3A-3C depict a fill assembly that may be included in a valve shut-off system, according to an embodiment.
Figure 3B:
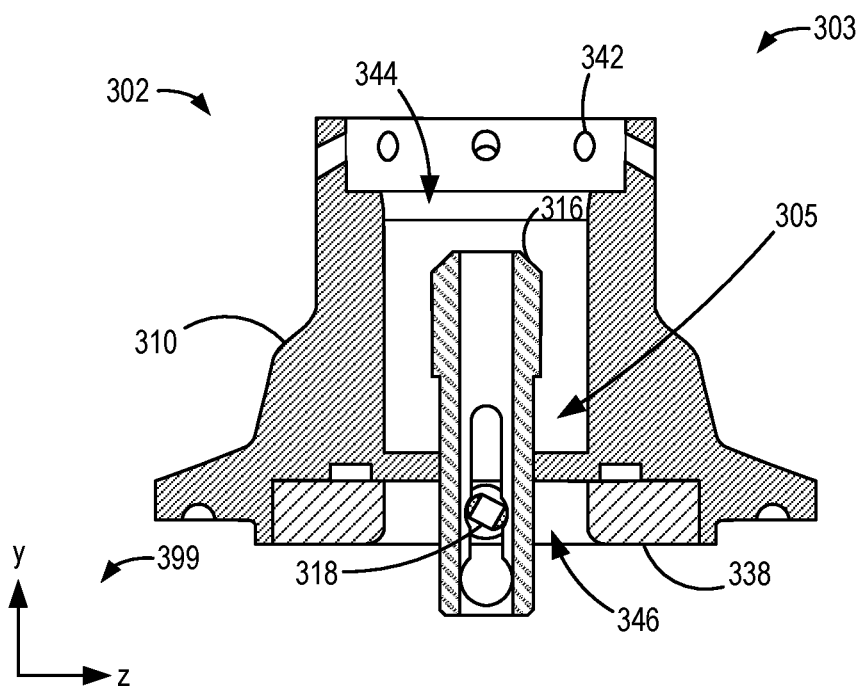
Figure 3C:
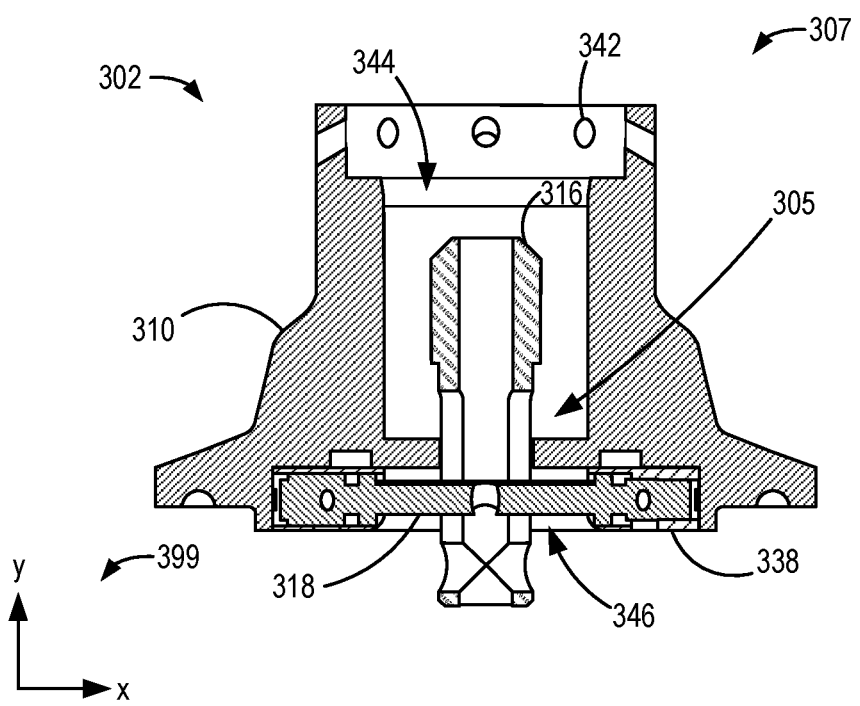

Turning now to FIGS. 3A-3C, an embodiment of a fill assembly 302 is shown. The fill assembly 302 is one embodiment of the fill assembly 102 of FIGS. 1A-1D, for example, and may be included in the valve shut-off system 100 of FIGS. 1A-1D or the valve shut-off system 200 of FIG. 2. Thus, components of FIGS. 3A-3C that correspond to components introduced in FIGS. 1A-1D and FIG. 2 are numbered similarly (e.g., 302 of FIGS. 3A-3C corresponds to 102 of FIGS. 1A-1D) and function as previously described. Further, reference axes 399 are provided to compare the relative orientation of the views shown in FIGS. 3A-3C. In particular, FIG. 3A shows an exploded view 300 of the fill assembly 302, FIG. 3B shows a first cross-sectional view 303 of the fill assembly 302 (e.g., in the z-y plane, as shown by reference axes 399), and FIG. 3C shows a second cross-sectional view 307 of the fill assembly 302 (e.g., in the x-y plane).

The fill assembly 302 includes a fill neck 310 having a central cavity 344 therein. The fill neck 310 further includes a plurality of vent holes 342, which allow fluidic communication between the central cavity 344 and an exterior of the fill neck 310. For example, the vent holes 342 may prevent pressure or vacuum from forming in the central cavity 344 when a refill bottle (not shown in FIGS. 3A-3C) is inserted or withdrawn from the fill neck 310. An overfill ring 338 interlocks with a bottom portion of the fill neck 310. For example, as particularly shown in FIGS. 3B and 3C, the overfill ring 338 may be encircled by the bottom portion of the fill neck 310.

The fill assembly 302 further includes a slide pin 316 and a rotating pin 318, which are included in an overfill prevention mechanism 305 (see FIGS. 3B and 3C). In the embodiment shown, the rotating pin 318 is at least partially housed within the overfill ring 338. As shown in FIG. 3A, the overfill ring 338 includes an insertion opening 340 sized to receive the rotating pin 318. Further, as shown in FIGS. 3B and 3C, the rotating pin 318 extends through a slot (e.g., opening) in the slide pin 316, perpendicular to a length of the slide pin 316. The geometries of the slide pin 316 and the rotating pin 318 will be further described below with respect to FIGS. 4A-6B. Because the rotating pin 318 is housed within the overfill ring 338, the rotating pin 318 is vertically (e.g., with respect to the y-direction of reference axes 399) and laterally (e.g., with respect to x- and z-directions of reference axes 399) fixed with respect to the other components of the fill assembly 302, including the slide pin 316. However, the rotating pin 318 is rotatable within the slot in the slide pin 316, forming a rotary joint with the slide pin 316.

The slide pin 316 is partially housed within the central cavity 344 of the fill neck 310, extending from the central cavity 344 and through a central opening 346 of the overfill ring 338. A bottom portion of the slide pin 316 extends below a bottom-most surface of the fill neck 310, such as into an interior of a reservoir on which the fill assembly 302 is installed. Note that although not shown in FIGS. 3A-3C, a fill assembly valve may be positioned below the slide pin 316, with a neck of the fill assembly valve extending up through slots within the overfill ring 338 into the central cavity 344 of the fill neck 310.

The rotating pin 318 is shown in the locked position in FIGS. 3B and 3C, where the slide pin 316 is held in the extended position, as introduced above with respect to FIGS. 1A-1C. With the slide pin 316 locked in the extended position by the rotating pin 318, the slide pin 316 may not move to the retracted position introduced above with respect to FIG. 1D. However, when the rotating pin 318 is actuated to the unlocked position where the slide pin 316 is not held in the extended position, the slide pin 316 may move vertically (e.g., with respect to the y-axis of reference axes 399). In particular, due to an effect of gravity and/or a bias spring of a refill bottle valve (not shown), the slide pin 316 may move in the negative y-direction until the rotating pin 318 reaches a top surface of the slot of the slide pin 316 and/or a flanged portion of the slide pin 316 (further described below with respect to FIGS. 4A-4B) contacts a bottom surface of the central cavity 344, referred to herein as the retracted position. Thus, a distance that the slide pin 316 extends into the central cavity 344 is greater in the extended position and smaller in the retracted position.

Figure 4A:
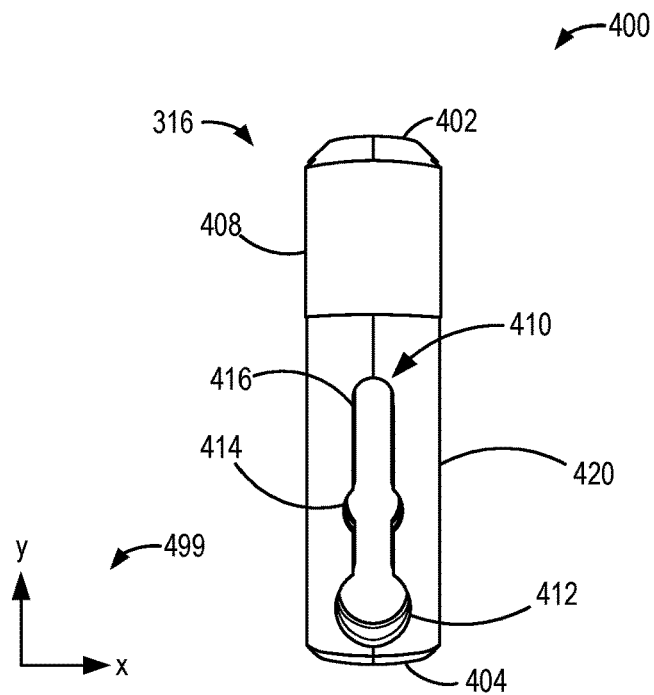
FIGS. 4A and 4B show a slide pin that may be included in a fill assembly of a valve shut-off system, according to an embodiment.
Figure 4B:
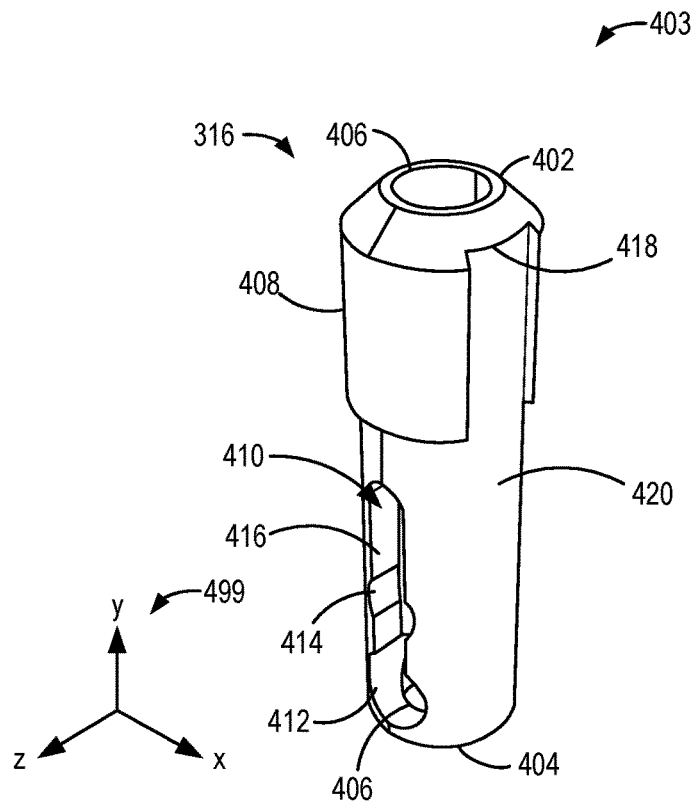

Continuing to FIGS. 4A and 4B, isolated views of the slide pin 316 introduced in FIGS. 3A-3C are shown. Reference axes 499 are included to compare the relative orientation of the slide pin 316 between a first view 400 shown in FIG. 4A and a second view 403 shown in FIG. 4B. In particular, FIG. 4A shows a front perspective view of the slide pin 316, and FIG. 4B shows an isometric perspective view of the slide pin 316.

The slide pin 316 includes a first end 402 and a second end 404 and a cylindrical body 420. The slide pin 316 further includes a central opening 406 that ends through a longitudinal axis of the cylindrical body 420 (e.g., in the y-direction of reference axes 499), a top of which is shown in FIG. 4B. Thus, the slide pin 316 includes a hollow interior. Further, the slide pin 316 has reflective and rotational symmetry about the longitudinal axis. The slide pin 316 includes a flange 408 proximate to the first end 402, which is wider than the cylindrical body 420. As shown in FIG. 4B, the flange may include at least one groove 418. The at least one groove 418 may be shaped to fit with a surface of a fill assembly valve stem (e.g., the fill assembly valve stem 115 of FIGS. 1A-1D), for example. The slide pin 316 further includes a mating slot 410 that extends transversely through the cylindrical body 420 (e.g., in the z-direction of reference axes 499), perpendicular to the longitudinal axis of the cylindrical body 420. The mating slot 410 is a lock-like opening having a locking geometry to which the rotating pin 318 (not shown in FIGS. 4A and 4B) is keyed, as will be elaborated below with particular reference to FIGS. 6A and 6B. Thus, the mating slot 410 may be referred to as a locking slot, and the rotating pin 318 has a geometry that mates with the locking slot (e.g., a mating geometry).

The mating slot 410 includes an insertion portion 412, a locking portion 414, and a sliding portion 416. The insertion portion 412 comprises the bottom-most portion of the mating slot 410, and is a circular opening where the mating slot 410 is the widest. The locking portion 414 of the mating slot 410 is positioned above the insertion portion 412 (with respect to the page and the orientation shown in FIGS. 4A and 4B). The locking portion 414 comprises a circular opening that is narrower than the insertion portion 412. Further, the locking portion 414 is connected to the insertion portion by an opening having parallel sides and a width that is less than the width (e.g., diameter) of the locking portion 414 and the width (e.g., diameter) of the insertion portion 412. For example, the insertion portion 412 may be sized to receive the rotating pin 318 (not shown in FIGS. 4A and 4B) during assembly, whereas the locking portion 414 may be sized to engage with and directly contact (e.g., lock with) the rotating pin 318 when the rotating pin 318 is in the locked position in order to prevent movement of the slide pin 316 in the positive and negative y-directions of reference axes 499.

The sliding portion 416 comprises the top-most portion of the mating slot 410. The sliding portion 416 includes parallel sides and is narrower than the locking portion 414 and the insertion portion 412. The sliding portion 416 may be sized to receive the rotating pin 318 (not shown in FIGS. 4A and 4B) when the rotating pin 318 is in the unlocked position and not while the rotating pin is in the locked position. Because the sliding portion 416 enables the slide pin 316 to move (e.g., slide) between the extended position and the retracted position, the sliding portion 416 may be referred to herein as having sliding geometry, in contrast to the locking geometry of the locking portion 414.

Figure 5A:
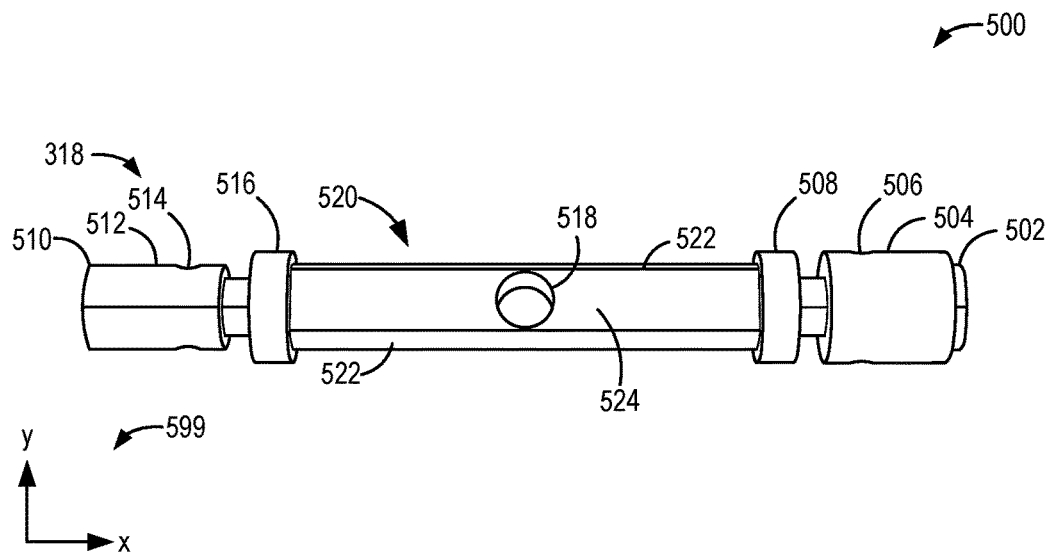
FIGS. 5A and 5B show a rotating pin that may be included in a fill assembly of a valve shut-off system, according to an embodiment.
Figure 5B:
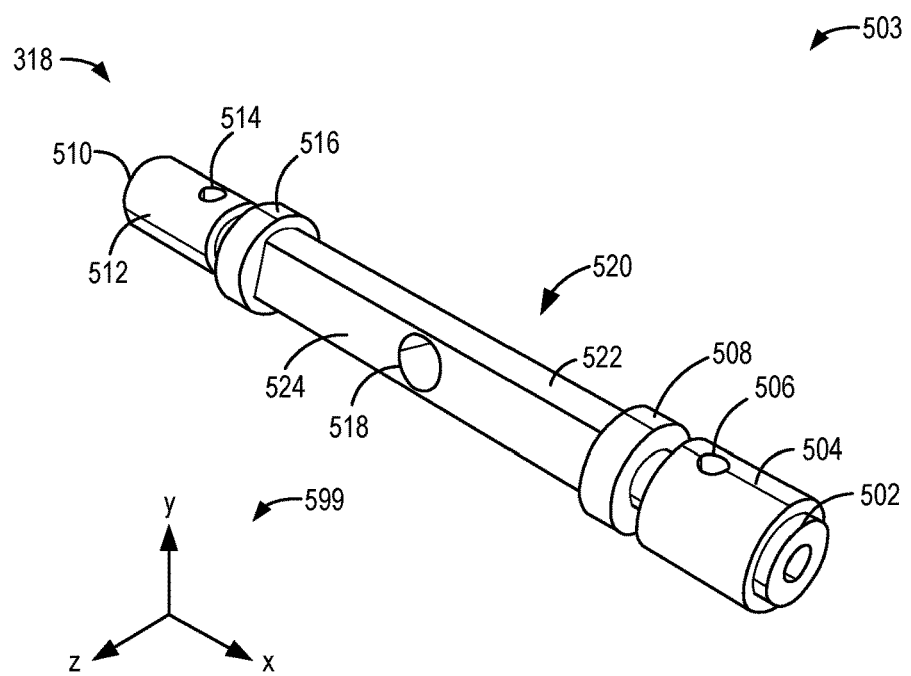
Figure 6A:
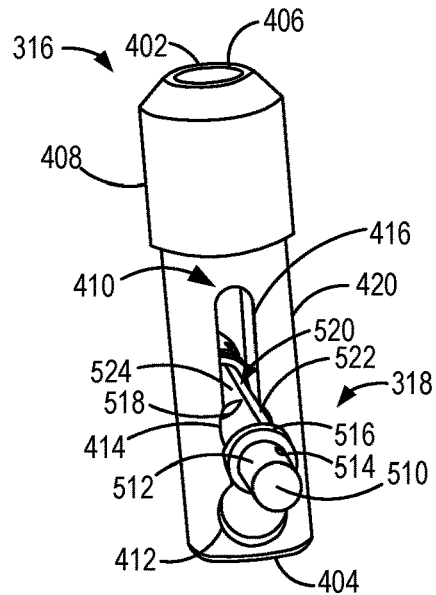
FIGS. 6A and 6B show a locked position and an unlocked position, respectively, of the rotating pin of FIGS. 5A-5B within the slide pin of FIGS. 4A-4B, according to an embodiment.
Figure 6B:
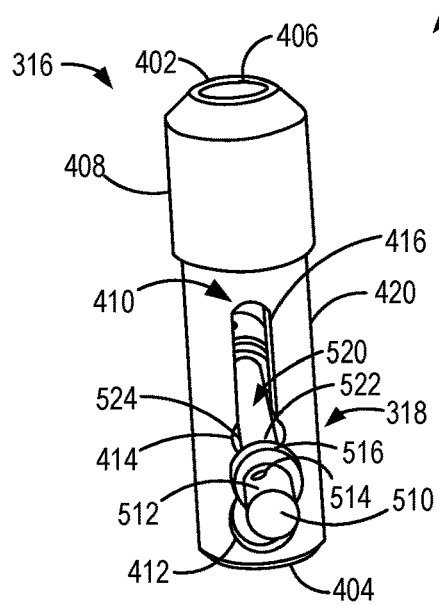

Referring now to FIGS. 5A and 5B, isolated views are shown of the rotating pin 318 introduced in FIGS. 3A-3C. Reference axes 599 are included to compare the relative orientation of the rotating pin 318 between a first view 500 shown in FIG. 5A and a second view 503 shown in FIG. 5B. In particular, FIG. 5A shows a front perspective view of the rotating pin 318, and FIG. 5B shows an isometric perspective view of the rotating pin 318. Further, the rotating pin 318 includes reflective and rotational symmetry about a longitudinal axis of the rotating pin 318 that is parallel to the x-axis of reference axes 599.

The rotating pin 318 includes a first end 502 having a first end cap 504. As particularly shown in FIG. 5B, the first end cap 504 includes a first coupling hole 506. The first coupling hole 506 provides a first coupling location for a mechanical linkage to an actuator (e.g., the mechanical linkage 122 to the actuator 120 shown in FIGS. 1A-1D) and extends through the first end cap 504 in the y-direction of reference axes 599, perpendicular to a length of the rotating pin (e.g., in the x-direction of reference axes 599). A first end stop 508 is positioned proximate to the first end cap 504. A first o-ring may be positioned in a groove formed between the first end stop 508 and the first end cap 504 in order to provide a seal between the rotating pin 318 and another surface within the fill assembly 302 (e.g., overfill ring 338, not shown in FIGS. 5A and 5B), for example. The first end stop 508 may have a same diameter as the first end cap 504, at least in some examples. The rotating pin 318 further includes a second end 510 opposite the first end 502, across the length of the rotating pin 318. The second end includes a second end cap 512 having a second coupling hole 514. The second coupling hole 514 provides a second coupling location for the mechanical linkage to the actuator and extends through the second end cap 512 in the y-direction of reference axes 599. Thus, the rotating pin 318 may be mechanically linked to the actuator via one or both of the first coupling hole 506 and the second coupling hole 514.

A second end stop 516 is positioned proximate to the second end cap 512. A second o-ring may be positioned in a groove formed between the second end stop 516 and the second end cap 512 in order to provide a seal between the rotating pin 318 and another surface within the fill assembly 302 (e.g., overfill ring 338, not shown in FIGS. 5A and 5B), for example. In the embodiment shown in FIGS. 5A and 5B, the second end stop 516 has a greater diameter than the second end cap 512 and a same diameter as the first end stop 508 and the first end cap 504. Because the second end cap 512 is sized differently than the first end stop 508, the rotating pin 318 is not symmetric about a vertical axis of the rotating pin 318 that is parallel the y-axis of reference axes 599.

A mating surface 520 is positioned between the first end stop 508 and the second end stop 516. The mating surface 520 includes a locking portion 522 on either side of the mating surface 520 in the y-direction and a sliding portion 524 on either side of the mating surface 520 in the z-direction. Referring to the orientation shown in FIGS. 5A and 5B, the locking portion 522 at the top of the rotating pin 318 includes a first arched surface that curves outward in the positive y-direction, and the locking portion 522 at the bottom of the rotating pin 318 includes a second arched surface that curves outward in the negative y-direction. The sliding portion 524 includes planar surfaces that are parallel to each other across a width of the rotating pin 318 (e.g., in the z-direction of reference axes 599). Further, a central opening 518 extends from a first side of the sliding portion 524 to a second side of the sliding portion 524 across the width of the rotating pin 318, perpendicular to the longitudinal axis of the rotating pin 318. The central opening 518 may help facilitate gas (e.g., vapor) and liquid exchange through the central opening 406 of the slide pin 316 (see FIGS. 4A and 4B). For example, the central opening 518 may be sized and positioned to maintain desired fill rates during a refilling operation. The rotating pin 318 is wider across the locking portion 522 (e.g., from the first arched surface to the second arched surface) than across the sliding portion 524 (e.g., between the planar surfaces). As such, the rotating pin 318 may fit differently within the mating slot 410 of the slide pin 316 (not shown in FIGS. 5A and 5B) depending on a rotational angle of the rotating pin 318 within the mating slot 410.

Next, FIGS. 6A and 6B show isolated views of the rotating pin 318 inserted within the slide pin 316. As such, components previously introduced in FIGS. 3A-5B are numbered the same and will not be re-introduced. FIG. 6A shows a first view 600 where the rotating pin 318 is in the locked position introduced above with respect to FIGS. 1A-1D, and FIG. 6B shows a second view 603 where the rotating pin 318 is in the unlocked position introduced above with respect to FIGS. 1A-1D. Further, some components of the rotating pin 318 are obscured in the views shown in FIGS. 6A and 6B and are therefore not labeled.

When inserted within the slide pin 316, the rotating pin 318 extends through the mating slot 410, with at least a portion of the mating surface positioned inside of the slide pin 316. For example, the rotating pin 318 may be inserted via the insertion portion 412 of the mating slot 410, which has a wider diameter than each of the first end cap 504, the first end stop 508, the second end cap 512, and the second end stop 516, for example. After insertion into the insertion portion 412, the rotating pin 318 may be rotated to the unlocked position (e.g., the orientation shown in FIG. 6B) in order to slide the rotating pin 318 from the insertion portion 412 of the mating slot 410 to the locking portion 414 via the narrower connection slot between the insertion portion 412 and the mating slot 410. After the slide pin 316 and the rotating pin 318 are installed in the fill assembly 302 (not shown in FIGS. 6A and 6B), however, the rotating pin 318 may not return to the insertion portion 412 and may instead travel between the locking portion 414 and the sliding portion 416 depending on the rotational position of the rotating pin 318, as will be elaborated below.

Referring first to FIG. 6A, the rotating pin 318 is positioned within the locking portion 414 of the mating slot 410 in the locked position. In the locked position, the second coupling hole 514 is rotated approximately 45° from the longitudinal axis of the slide pin 316 that extends from the first end 402 to the second end 404. Further, the arched surfaces of the locking portion 522 of the mating surface 520 are in direct contact with an inner surface of the locking portion 414 of the mating slot 410. Because the mating surface 520 is in direct contact with the locking portion 414 of the mating slot 410 and the sliding portion 416 of the mating slot 410 is narrower than the locking portion 414, the rotating pin 318 does not fit into the sliding portion 416 of the mating slot 410 when in the locked position. Further, the rotating pin 318 does not fit into the mating slot 410 between the insertion portion 412 and the locking portion 414. Thus, the rotating pin 318 is not moveable between the different portions of the mating slot 410 when the rotating pin 318 is in the locked position.

Referring next to FIG. 6B, the rotating pin 318 is positioned within the locking portion 414 in the unlocked position. In the unlocked position, the second coupling hole 514 is approximately parallel to the longitudinal axis of the slide pin 316 (e.g., rotated from the longitudinal axis of the slide pin 316 by a smaller degree than in the locked position). Further, the planar surfaces of the sliding portion 524 of the mating surface 520 are parallel to the parallel sides of the sliding portion 416 of the mating slot 410. With the rotating pin 318 in the unlocked position, the mating surface 520 is no longer in contact with the inner surface of the locking portion 414 of the mating slot 410. The width of the rotating pin 318 between the planar surfaces of the sliding portion 524 is sized to fit within the sliding portion 416 of the mating slot 410. Thus, the slide pin 316 may slide along the rotating pin 318 so that the rotating pin 318 is positioned within the sliding portion 416 of the mating slot 410, as will be further described below with respect to FIG. 7B.

Further, the first end stop 508 and the second end stop 516 are wider than the locking portion 414. Thus, even when the mating surface 520 is disengaged from the inner surface of the mating slot 410, a lateral movement of the rotating pin 318 (e.g., with respect to the longitudinal axis of the slide pin 316) is restricted by the position of the first end stop 508 and the second end stop 516.

Figure 7A:
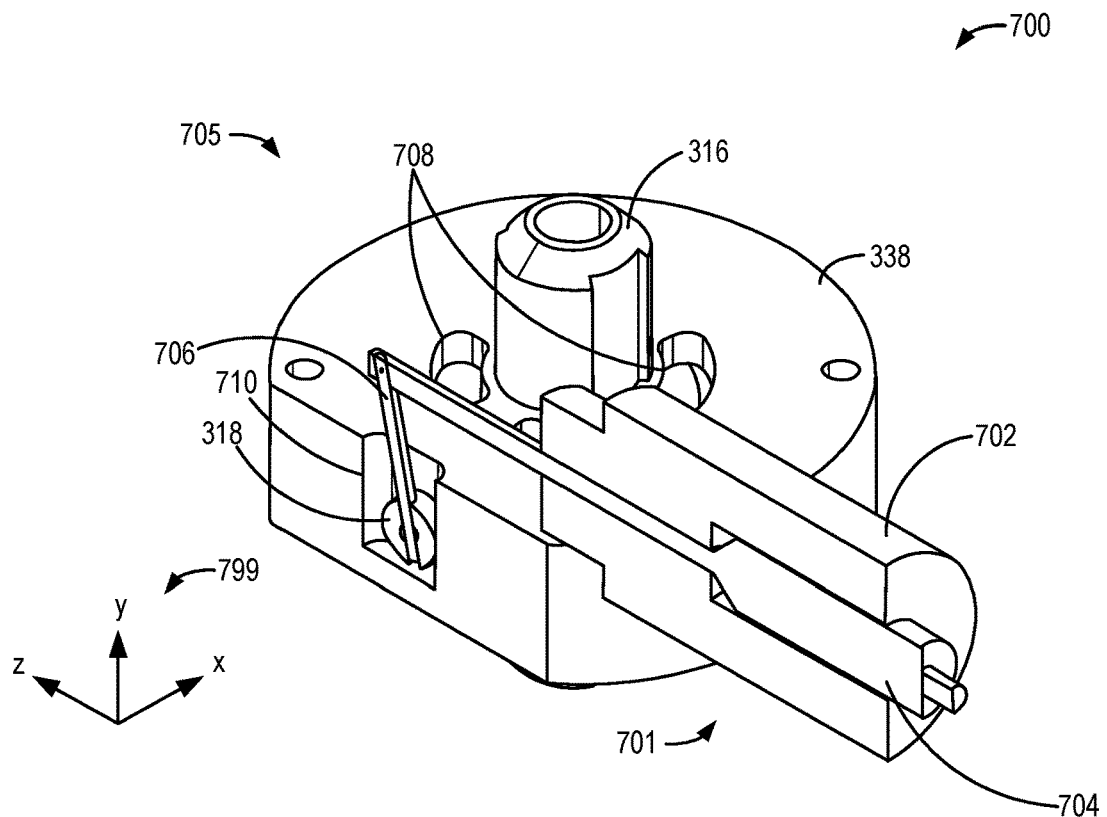
FIGS. 7A and 7B show partial views of an electro-mechanical actuator that may be included in a valve shut-off system, according to an embodiment.
Figure 7B:
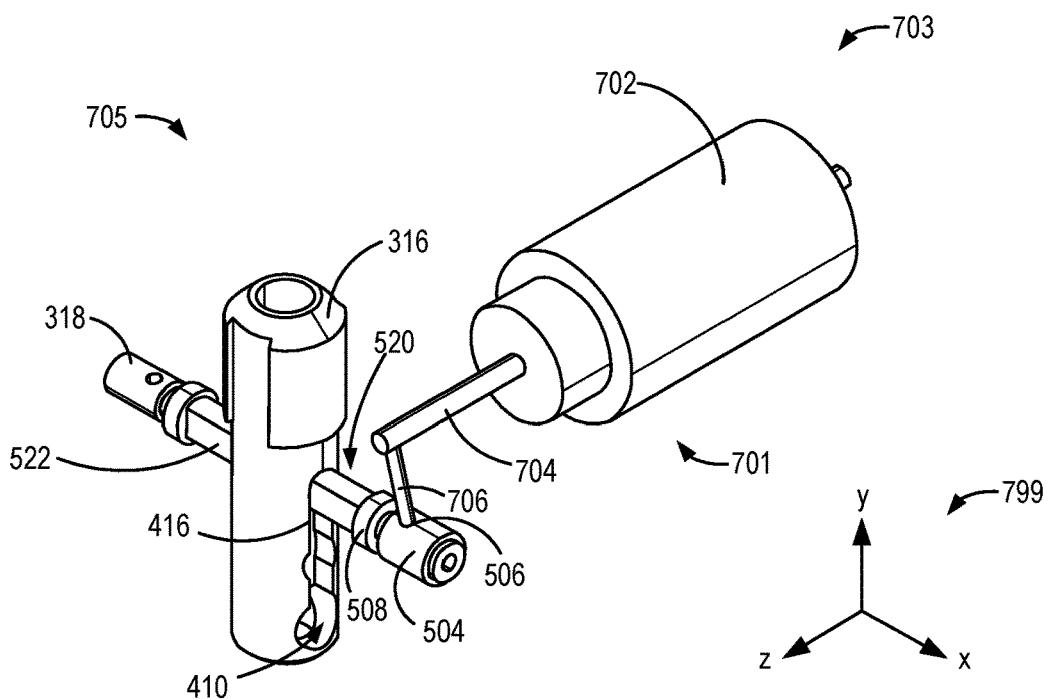

Turning now to FIGS. 7A and 7B, an embodiment of an overfill prevention mechanism 705 that includes an electromechanical actuator is shown. Thus, the overfill prevention mechanism 705 may be one embodiment of the overfill prevention mechanism 105 of the valve shut-off system 100 of FIGS. 1A-1D. Components of FIGS. 7A and 7B that have already been introduced with respect to FIGS. 3A-5B are numbered the same and will not be reintroduced. Further, some components of the slide pin 316 and the rotating pin 318 are not labeled in FIGS. 7A and 7B for illustrative clarity. FIG. 7A shows a cross-sectional isometric perspective view 700, and FIG. 7B shows an isometric perspective view 703. Further still, reference axes 799 are included to compare the relative orientation of the components in the two views.

The overfill prevention mechanism 705 includes a solenoid 701 having a solenoid coil 702 and a solenoid shaft 704. The solenoid 701 is one embodiment of the actuator 120 of FIGS. 1A-1D, for example. A position of the solenoid shaft 704 relative to the solenoid coil 702 is adjusted based on an energization state of the solenoid 701 (e.g., by energizing or de-energizing solenoid coil 702), as will be elaborated below with reference to FIGS. 8A-8C and FIG. 11. For example, the solenoid shaft 704 may extend a further distance from the solenoid coil 702 when the solenoid coil 702 is de-energized, and the solenoid shaft 704 may be pulled further into the solenoid coil 702 when then solenoid coil 702 is energized. The solenoid coil 702 may be an electromagnetically inductive coil that creates a magnetic field when energized, and the solenoid shaft 704 may be a magnetic (e.g., ferromagnetic) plunger that is pulled into (or pushed out of) a center of the solenoid coil 702 due to a force applied by the magnetic field.

The cross-section shown in FIG. 7A bisects the solenoid coil 702 and the solenoid shaft 704. The solenoid shaft 704 is mechanically coupled to the rotating pin 318 via a mechanical linkage 706, which may be the mechanical linkage 122 of FIGS. 1A-1D, for example. In the embodiment shown, the mechanical linkage 706 is coupled to the solenoid shaft 704 at a first end, forming a moveable joint with the solenoid shaft 704, and coupled to the rotating pin via the first coupling hole 506. For example, the mechanical linkage 706 may be friction-fit within the first coupling hole 506, bonded with the first coupling hole 506, or otherwise secured.

Further, the cross-sectional isometric perspective view 700 of in FIG. 7A shows the overfill ring 338. The overfill ring 338 is shown including a slot 708 shaped to allow liquid medical agent, vapor, and gas to pass between the fill assembly and the refill bottle and a groove 710 that enables movement of the mechanical linkage 706. For example, as the solenoid shaft 704 is pulled out or pushed in relative to the solenoid coil 702, an angle of the mechanical linkage 706 changes with respect to an axis parallel to the y-axis of reference axes 799 and perpendicular to the longitudinal axis of the rotating pin 318. As the angle of the mechanical linkage 706 changes, the rotating pin 318 is rotated about an axis of rotation, parallel to its longitudinal axis and parallel to the x-axis of reference axes 799. Further, because the mechanical linkage 706 is positioned outside of a reservoir (e.g., medical device reservoir 104 of FIGS. 1A-1D), an o-ring positioned in the groove between the first end cap 504 and the first end stop 508 may form a vapor- and liquid-tight seal with the overfill ring 338 proximate to the groove 710. As such, medical agent may be kept inside the reservoir.

The rotating pin 318 is in the unlocked position in the views shown in FIGS. 7A and 7B. As particularly shown in FIG. 7B, in the unlocked position, the planar surfaces of the sliding portion 524 of the mating surface 520 are parallel to the parallel sides of the sliding portion 416 of the mating slot 410. As a result, the rotating pin 318 is positioned within the sliding portion 416 of the mating slot 410.

Continuing to FIGS. 8A-8C, actuation of the overfill prevention mechanism 705 to adjust the slide pin 316 between the extended position and the retracted position will now be described in the context of other components of the fill assembly 302 introduced in FIGS. 3A-3C. As such, components previously introduced in FIGS. 3A-7B are numbered the same and will not be re-introduced. Although reference axes are not shown, it may be understood that the views of FIGS. 8A-8C are in a same cross-sectional plane. Further, although labeled for context, some components will not be referenced with respect to FIGS. 8A-8C.

Turning first to a first view 800 shown in FIG. 8A, the solenoid shaft 704 is in a first, pushed out position relative to the solenoid coil 702. For example, the solenoid shaft 704 may be pushed out by a return spring (not shown) when the solenoid coil 702 is de-energized. With the solenoid shaft 704 in the first position, the rotating pin 318 is in the locked position within the slide pin 316, holding the slide pin 316 in the extended position via direct contact (e.g., engagement) between the mating surface 520 of the rotating pin (specifically, the locking portion 522 of the mating surface 520) and the mating slot 410 of the slide pin 316 (specifically, the locking portion 414 of the mating slot 410). Thus, the slide pin 316 may engage with and open a refill bottle valve (not shown), as described above with respect to FIG. 1C and as will be further elaborated below with respect to FIG. 9A.

Continuing to a second view 803 shown in FIG. 8B, the solenoid shaft 704 is in a second, pulled in position relative to the solenoid coil 702. For example, the solenoid shaft 704 may be pulled further into the center of the solenoid coil 702, against a spring force of the return spring, by a force from magnetic field applied on the solenoid shaft 704 by the solenoid coil 702 when the solenoid coil 702 is energized. As a result of the solenoid shaft 704 movement, the rotating pin 318 is adjusted to the unlocked position, disengaging the locking portion 522 of the mating surface 520 from the locking portion 414 of the mating slot 410. As a result, the slide pin 316 is no longer held in the extended position and is moveable relative to the rotating pin 318.

Due to gravity and/or a force applied by the refill bottle valve (not shown) while the solenoid shaft 704 is pushed in and the rotating pin 318 is in the unlocked position, the slide pin moves to the retracted position shown in a third view 805 of FIG. 8C. In the retracted position, the sliding portion 524 of the mating surface 520 may contact the sliding portion 416 of the mating slot 410. As shown, the slide pin 316 may slide relative to the rotating pin 318 until the rotating pin 318 contacts a top inner surface of the mating slot 410 and/or a bottom surface of the flange 408 of the slide pin 316 contacts a top surface of the overfill ring 338.

Next, FIGS. 9A and 9B show an example sequence 900 of operating a valve shut-off system to enable and disable flow between a refill bottle 906 and a reservoir 904. The valve shut-off system may be the valve shut-off system 100 of FIGS. 1A-1D or the valve shut-off system 200 of FIG. 2, for example. FIGS. 9A and 9B will be described with respect to the fill assembly 302 introduced in FIGS. 3A-3C, including the overfill prevention mechanism 305. As such, components previously introduced in FIGS. 3A-3C are numbered the same and will not be re-introduced. The sequence 900 is shown with respect to time, with time increasing along a time axis 901 in the direction of the arrow. Distinct time points of the sequence 900 will be described. It may be appreciated that a variable amount of time may pass between each time point of the sequence 900, and the time axis 901 is meant to denote an order of each time point in the sequence 900 and is not meant to denote an amount of time between each time point.

At a first time point t1, a refill bottle neck 924 of the refill bottle 906 is partially inserted into the fill neck 310 of the fill assembly 302, which is positioned on an external surface of the reservoir 904. The refill bottle neck 924 is shown contacting a fill assembly valve stem 915 of a fill assembly valve 912. However, the refill bottle neck 924 is not yet inserted enough to open the fill assembly valve 912 at the first time point t1. Therefore, the fill assembly valve 912 is closed, with a fill assembly valve seal 914 in direct contact with a surface of the overfill ring 338. For example, the fill assembly valve 912 may be held closed by a bias spring (e.g., the bias spring 138 of FIGS. 1A-1D).

Also at the first time point t1, the rotating pin 318 is in the locked position within the rotating pin 318. As a result, the slide pin 316 is held in the extended position relative to the reservoir 904. However, the refill bottle neck 924 is not yet inserted enough for the slide pin 316 to engage with a refill bottle valve stem 925 of a refill bottle valve 926. Therefore, the refill bottle valve 926 is closed, with a refill valve seal 928 in direct contact with a surface of the refill bottle neck 924. For example, the refill bottle valve 926 may be held closed by a bias spring (e.g., the bias spring 140 shown in FIGS. 1A-1D).

At a second time point t2, the refill bottle neck 924 is further inserted into the fill neck 310. The refill bottle neck 924 opens the fill assembly valve 912 (e.g., the refill bottle neck 924 is inserted by at least the first distance described above with respect to FIGS. 1A-1D). With the fill assembly valve 912 open, the fill assembly valve seal 914 is no longer in contact with the overfill ring 338, and an interior of the reservoir 904 is fluidically coupled to the refill bottle neck 924. The slide pin 316, which remains in the extended position by the locked rotating pin 318, begins engage with the refill bottle valve stem 925, but the refill bottle neck 924 is not yet inserted enough for the slide pin 316 to open the refill bottle valve 926 (e.g., the refill bottle neck 924 is inserted by less than the second distance described above with respect to FIGS. 1A-1D). Thus, the refill bottle valve 926 remains closed, and the refill bottle 906 is not fluidically coupled to the refill bottle neck 924. Thus, the refill bottle 906 is not fluidically coupled to the reservoir 904 even though the fill assembly valve 912 is open.

At a third time point t3, the refill bottle neck 924 is fully inserted within the fill neck 910. In the fully inserted position, the refill bottle neck 924 directly contacts a surface at a bottom of the central cavity 344 (see FIGS. 3A-3C) of the fill neck 310. The fill assembly valve 912 is further opened at the third time point t3 than at the second time point t2. For example, a degree to which the fill assembly valve 912 is opened may be proportional to an insertion distance of the refill bottle neck 924 (e.g., once the first distance is reached). The slide pin 316 remains locked in the extended position by the rotating pin 318 and opens the refill bottle valve 926. Thus, the refill bottle 906 is fluidically coupled to the reservoir 904, and medical agent (not shown in FIGS. 9A and 9B) may flow from the refill bottle 906 to the reservoir 904. Further, once the slide pin 316 engages with the refill bottle valve stem 925 and begins to open the refill bottle valve 926 (e.g., once the second distance is reached), a degree to which the refill bottle valve 926 is opened may be proportional to the insertion distance of the refill bottle neck 924 in the fill neck 310 until the fully inserted position is reached.

At a fourth time point t4, the rotating pin 318 is adjusted to the unlocked position by an actuator (not shown), which may be actuator 120 of FIGS. 1A-1D, for example. As an example, the actuator may adjust the rotating pin 318 to the unlocked position responsive to an indication that the reservoir 904 is full (e.g., based on a level of the medical agent within the reservoir), a set timer elapsing, and/or manual actuation by a user. With the rotating pin 318 in the unlocked position, the slide pin 316 is no longer held in the extended position and thus, no longer holds open the refill bottle valve 926.

As a result, at a fifth time point t5 (see FIG. 9B), the slide pin 316 is adjusted to the retracted position, and the refill bottle valve 926 closes. For example, the slide pin 316 may be adjusted to the retracted position by a spring force of the bias spring of the refill bottle valve 926, which fully closes the refill bottle valve 926. Thus, even though the refill bottle neck 924 remains fully inserted within the fill neck 310 and the fill assembly valve 912 remains open at the fifth time point t5, the refill bottle 906 is no longer fluidically coupled to the reservoir 904, and the medical agent may no longer flow from the refill bottle 906 to the reservoir 904. However, any remaining medical agent within the refill bottle neck 924 and/or the fill neck 310 may continue to flow into the reservoir 904 via the open fill assembly valve 912.

At a sixth time point t6, the refill bottle neck 924 is being withdrawn from the fill neck 310. As a result, the fill assembly valve 912 begins to close. Further, the refill bottle valve stem 925 is no longer in contact with the slide pin 316. Thus, the slide pin 316 is no longer held in the retracted position by the bias spring of the refill bottle valve 926. As a result, the fill assembly valve 912 pushes the slide pin 316 back into the extended position. However, the rotating pin 318 remains in the unlocked position. Thus, the slide pin 316 is not held in the extended position, and if the refill bottle neck 924 were re-inserted into the fill neck 310, the slide pin 316 would move to the retracted position via a force from the refill bottle valve stem 925 and would not open the refill bottle valve 926.

At a seventh time point t7, the rotating pin 318 is adjusted to the locked position with the slide pin 316. As a result, the slide pin 316 is held in the extended position, and if the refill bottle neck 924 were re-inserted into the fill neck 310, the slide pin 316 would open the refill bottle valve 926. However, the refill bottle neck 924 is further removed from the fill neck 310, and at an eighth time point t8, the fill assembly valve 912 is fully closed.

Figure 10:
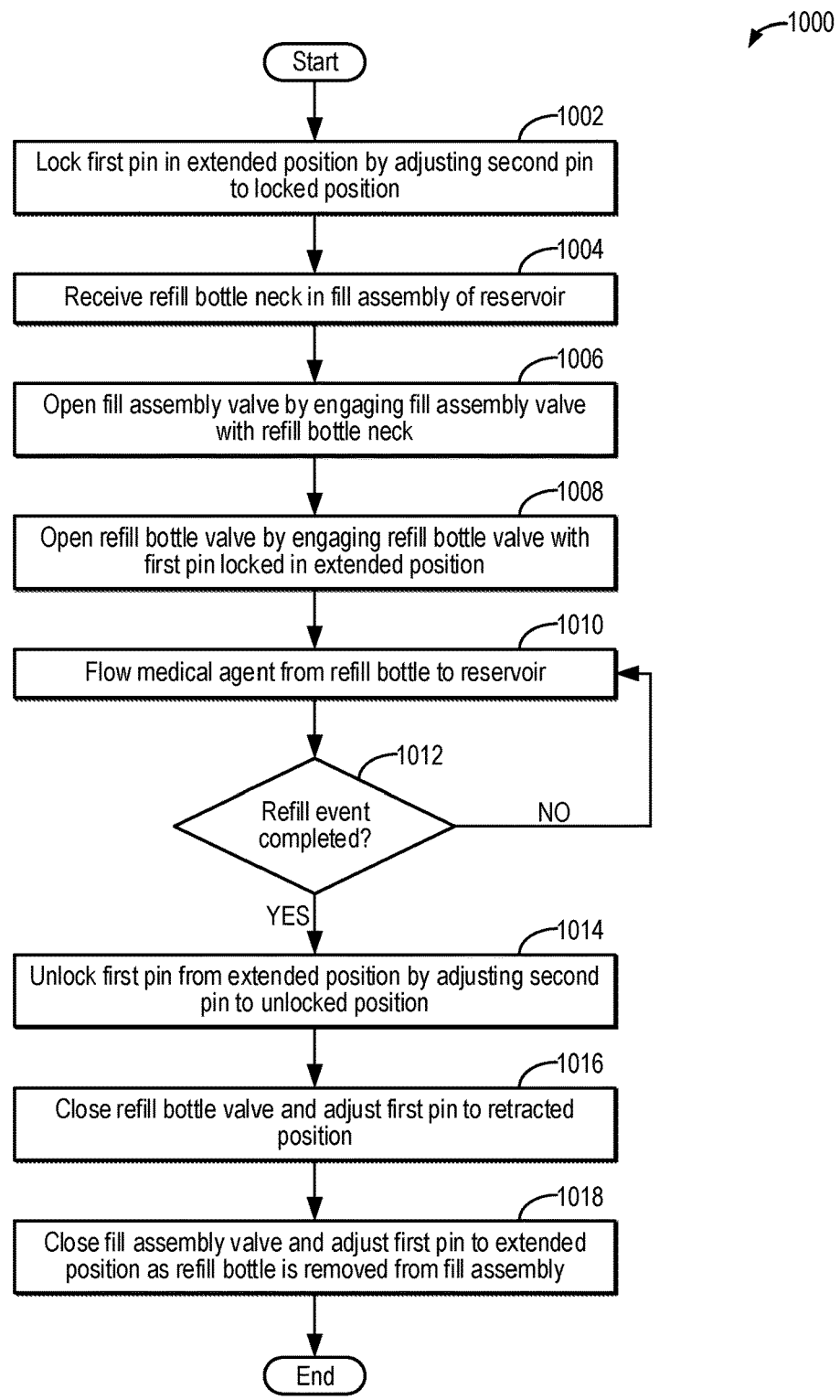
FIG. 10 shows a high-level flow chart of a method for operating a valve shut-off system to enable and disable flow between a refill bottle and a reservoir, according to an embodiment.
Figure 11:
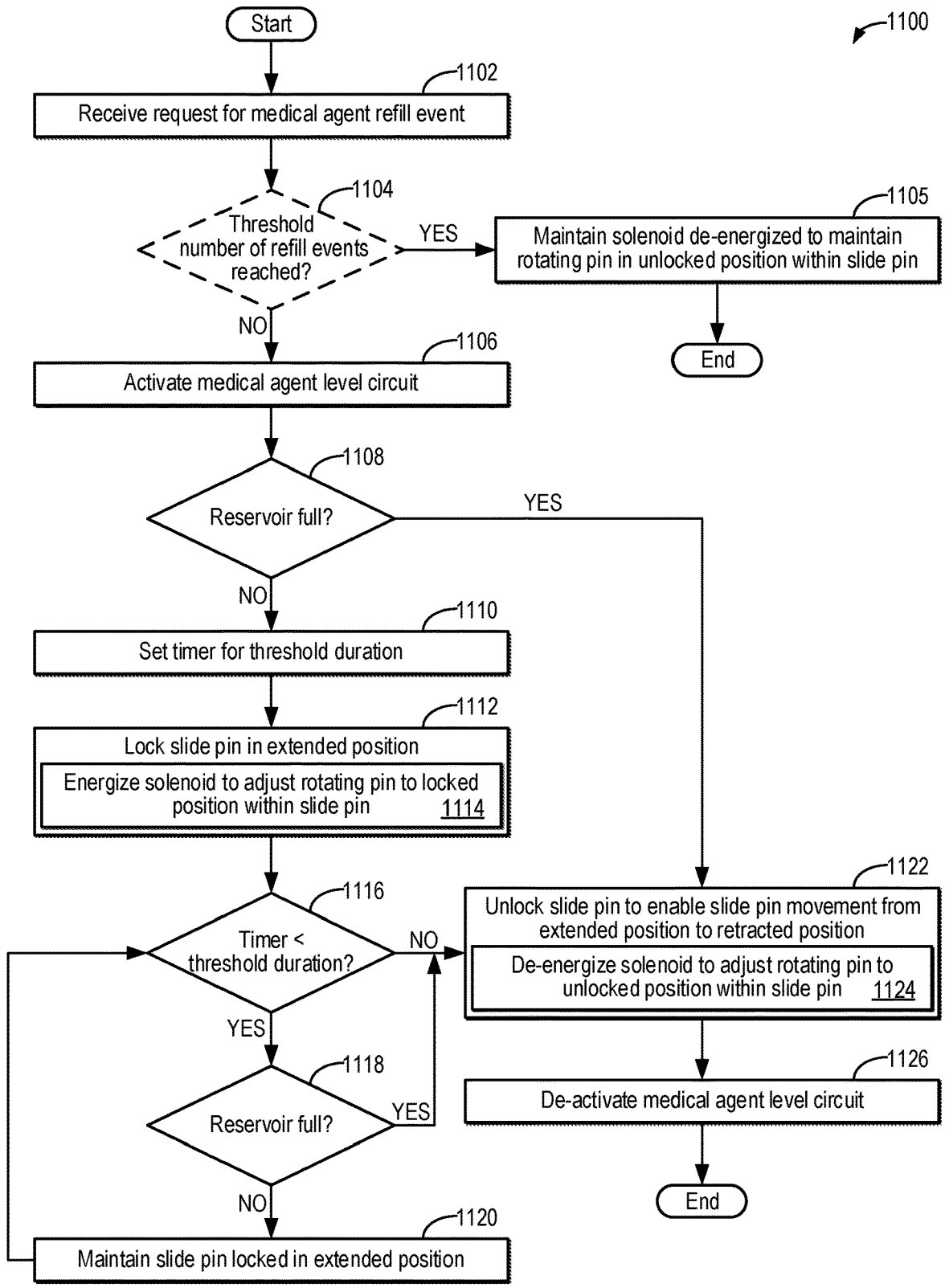
FIG. 11 shows a flow chart of a method for controlling an electro-mechanical actuator of a valve shut-off system to enable and disable flow between a refill bottle and a reservoir, according to an embodiment.

Turning now to FIG. 10, a high-level example method 1000 is provided for controlling flow between a refill bottle and a reservoir during a refill event using a valve shut-off system. The valve shut-off system may be the valve shut-off system 100 of FIGS. 1A-1D or the valve shut-off system 200 of FIG. 2, for example, and may include the overfill prevention mechanism 305 introduced in FIGS. 3A-3C. Further, reference will be made to the time points of the sequence 900 of FIGS. 9A and 9B. The method 1000 may be performed via mechanical control, electronic control, or a combination thereof. Thus, in some examples, at least parts of the method 1000 may be executed by a controller (e.g., the controller 130 of FIGS. 1A-1D) based on instructions stored in a memory of the controller.

At 1002, the method 1000 includes locking a first pin in an extended position by adjusting a second pin to a locked position. As shown in the first time point t1 of FIG. 9A, when the refill event is initiated and the reservoir is not full, the second pin (e.g., the rotating pin 318 introduced in FIGS. 3A-3C) may be adjusted to the locked position so that the first pin (e.g., the slide pin 316 of FIGS. 3A-3C) is positioned to engage with and open a refill bottle valve once a refill bottle neck of the refill bottle is inserted into a fill assembly of the reservoir. Thus, in such examples, the second pin may be adjusted to the locked position responsive to the initiation of the refill event. Alternatively, if the second pin is already in the locked position, the second pin may be maintained in the locked position. The locked position may include the second pin being in direct contact with a locking portion of a mating slot of the first pin, such as described above with particular reference to FIG. 6A.

Further, in some embodiments, the position of the second pin may be controlled based on a position of a mechanical actuator. In embodiments where the mechanical actuator is a buoyant float positioned in the reservoir (e.g., the float 220 of FIG. 2), the second pin may be held in the locked position when a level of the float is less than a threshold level, corresponding to a maximum desired amount (e.g., volume or level) of the medical agent within the reservoir (e.g., a level above which the reservoir is overfilled). In other embodiments where the position of the second pin is controlled via electronic actuation, such as using the solenoid 701 described with respect to FIGS. 7A-8C, a controller (e.g., the controller 130 of FIGS. 1A-1D) may adjust or maintain the position of the actuator to adjust or maintain the second pin in the locked position, such as responsive to a measured level of the medical agent within the reservoir being less than the threshold level.

At 1004, the method 1000 includes receiving a refill bottle neck of the refill bottle in a fill assembly of the reservoir. In particular, the refill bottle neck may be inserted within a fill neck of the fill assembly by a user. As also shown in the first time point t1 of FIG. 9A, the refill bottle neck may be inserted into a central cavity in the fill assembly, and a valve of the refill bottle may be initially maintained closed during the insertion.

At 1006, the method 1000 includes opening a fill assembly valve by engaging the fill assembly valve with the refill bottle neck. Referring to the second time point t2 of FIG. 9A, the refill bottle neck may open the fill assembly valve as the refill bottle is further inserted into the fill assembly. Further, the refill bottle valve may remain closed as the fill assembly valve begins to open. For example, the refill bottle neck may open the fill assembly valve against a bias spring of the fill assembly valve, such as described with respect to FIG. 1B.

At 1008, the method 1000 includes opening the refill bottle valve by engaging the refill bottle valve with the first pin locked in the extended position. In the extended position, the first pin extends a greater distance into the central cavity of the fill assembly, and thus a further distance toward the refill bottle valve. Further, with the second pin in the locked position, the first pin is held in the extended position and is not movable to a retracted position that is a smaller distance into the central cavity and a smaller distance toward the refill bottle valve. As a result, the first pin is positioned to open the refill bottle valve, such as shown in the third time point t3 of FIG. 9A. For example, the first pin may open the refill bottle valve against a bias spring of the refill bottle valve, such as described with respect to FIG. 1C.

At 1010, the method 1000 includes flowing the medical agent from the refill bottle to the reservoir. With the refill bottle valve open, the medical agent may flow from the refill bottle to the refill bottle neck, through the fill assembly, and into the reservoir via the open fill assembly valve, such as schematically shown in FIG. 1C.

At 1012, the method 1000 includes determining if the refill event is completed. As one example, the refill event may be considered completed responsive to a pre-determined duration elapsing. The pre-determined duration may be tracked by a mechanical or electronic timer that is started when the refill bottle is inserted, for example. As another example, additionally or alternatively, the refill event may be considered completed responsive to the medical agent in the reservoir reaching the threshold level described above at 1002, such as by the float reaching the threshold level or a level sensor indicating the level of the medical agent in the reservoir has reached the threshold level. As still another example, the refill event may be considered completed responsive to a user manually pushing a button, manually removing the refill bottle, or via another input.

If the refill event is not completed, the method 1000 returns to 1010 and continues to flow the medical agent from the refill bottle to the reservoir. Thus, fluid communication is maintained between the refill bottle and the reservoir until the refill event is completed.

If the refill event is completed, the method 1000 proceeds to 1014 and includes unlocking the first pin from the extended position by adjusting the second pin to the unlocked position. The second pin may be adjusted to the unlocked position via the actuator. As an example, when the refill event is completed, the position of the actuator may be such that the second pin is adjusted from the locked position to the unlocked position, such as shown in the fourth time point t4 of FIG. 9A. With the second pin in the unlocked position, the second pin is no longer in direct contact with the locking portion of the mating slot of the first pin. Thus, the first pin is no longer held in the extended position and is moveable to the retracted position.

At 1016, the method 1000 includes closing the refill bottle valve and adjusting the first pin to the retracted position. Because the first pin is no longer held in the extended position, the bias spring of the refill bottle valve both closes the refill bottle valve and pushes the first pin into the retracted position, such as described above with respect to FIG. 1D. Further, as shown in the fifth time point t5 of FIG. 9B, the fill assembly valve remains open after the refill bottle valve closes.

At 1018, the method 1000 includes closing the fill assembly valve and adjusting the first pin to the extended position as the refill bottle is removed from the fill assembly. As an example, the fill assembly valve may be closed by the bias spring of the fill assembly valve as the refill bottle is further removed until the fill assembly valve reaches a fully closed position, such as shown in the sixth time point t6 through the eighth time point t8 of FIG. 9B. Further, as the fill assembly valve closes, it may physically contact the first pin to push the first pin back into the extended position. However, the first pin may not be held in the extended position until the second pin is adjusted to the locked position. In some embodiments, the second pin may be maintained in the locked position as a default position between refill events. However, in other embodiments, the second pin may be maintained in the unlocked position as the default position between refill events. In still other embodiments, the second pin may not have a default position, and the position of the second pin may be adjusted between refill events based on the position of the actuator, such as when the actuator is a float in the reservoir. The method 1000 then ends. For example, the method 1000 may be repeated during a subsequent refill event.

Next, FIG. 11 shows a flow chart of an example method 1100 for controlling flow between a refill bottle and a reservoir via a valve shut-off system including an electro-mechanical actuator. The valve shut-off system may be the valve shut-off system 100 of FIGS. 1A-1D, for example, and may include the overfill prevention mechanism 705 including the solenoid 701 as the electro-mechanical actuator, as described with respect to FIGS. 7A-8C. Thus, while the method 1000 provides a high-level method for operating the valve shut-off system, the method 1100 provides a more specific electronic control method. As such, the method 1100 may be executed by a controller (e.g., the controller 130 of FIGS. 1A-1D) based on instructions stored in a memory of the controller. Further, at least parts of the method 1100 may be included in another control method, such as the method 1000 of FIG. 10.

At 1102, the method 1100 includes receiving a request for a medical agent refill event. For example, the medical agent refill event may be requested by a user, such as via a user input device electronically coupled to the controller (e.g., the user interface 135 of FIGS. 1A-1D). As another example, the user may depress a fill button electronically coupled to the controller. As still another example, a fill neck of the reservoir (e.g., the fill neck 310 shown in FIGS. 7A-8C) may include a sensor that detects insertion of a refill bottle neck within the fill neck. For example, in response to detecting that the refill bottle neck is inserted within the fill neck via the fill neck sensor, the controller may wake (e.g., activate) a medical agent level circuit, as will be elaborated below at 1106. Further, the fill neck sensor may determine whether the refill event is requested but not the filling state of the reservoir, as the filling state is controlled by the overfill prevention mechanism and does not directly correlate to whether or not the refill bottle is inserted. Thus, receiving the request for the medical agent refill event may include detecting insertion of the refill bottle neck by the fill neck sensor in some embodiments, and the controller may activate the overfill prevention mechanism and proceed to determine if filling is indicated based on a fill level of the reservoir measured by the medical agent level circuit.

At 1104, the method 1100 optionally includes determining if a threshold number of refill events has been reached. For example, the method 1100 may include 1104 when the solenoid receives electrical power from a super capacitor (e.g., when power source 132 of FIGS. 1A-1D comprises a super capacitor). Because each refill event uses electrical power, the threshold number of refill events may be a pre-determined, non-zero number of refill events between super capacitor charging events that is calibrated based on a size of the super capacitor in order to prevent the super capacitor from running out of power during the refill event. However, 1104 may not be included when the solenoid is powered by a battery or mains power, for example.

If the threshold number of refill events has been reached since the super capacitor has last been charged, the method 1100 proceeds to 1105 and includes maintaining the solenoid de-energized to maintain a rotating pin (e.g., the rotating pin 318 shown in FIGS. 7A-8C) in an unlocked position within a slide pin (e.g., the slide pin 316 shown in FIGS. 7A-8C). Thus, electric power (e.g., electrical current) is not supplied from the super capacitor to a solenoid coil of the solenoid (e.g., the solenoid coil 702 of FIGS. 7A-8C). As such, a solenoid shaft (e.g., the solenoid shaft 704 of FIGS. 7A-8C) remains pushed out with respect to the solenoid coil, thus maintaining the rotating pin in the unlocked position. With the rotating pin in the unlocked position, the slide pin is not held in an extended position for engaging with and opening a valve of the refill bottle. Therefore, even if the refill bottle neck is inserted into the fill neck, the slide pin will retract and will not open the refill bottle valve. As a result, medical agent will not enter the reservoir from the refill bottle. The method 1100 may then end.

If the threshold number of refill events is not reached, or if 1104 is omitted, the method 1100 proceeds to 1106 and includes activating the medical agent level circuit. The medical agent level circuit may include a level sensor positioned to measure or otherwise indicate a level (e.g., height, volume, or amount) of medical agent within the reservoir (e.g., the level sensor 133 of FIGS. 1A-1D). The medical agent level circuit may electronically communicate the level of medical agent within the reservoir to the controller, for example.

At 1108, the method 1100 includes determining if the reservoir is full. The reservoir may be considered full when the level of medical agent within the reservoir is greater than or equal to a threshold level, for example. The threshold level may be a pre-determined, non-zero medical agent level calibrated to maintain a desired head space above the medical agent within the reservoir, as elaborated above with respect to FIG. 2. Additionally or alternatively, the threshold level may be calibrated to reduce or prevent overfilling of the reservoir. The controller may determine if the reservoir is full based on the level of medical agent sensed or otherwise indicated by the level sensor, for example. In embodiments where the level sensor is a switch, the controller may determine that the reservoir is not full responsive to the level switch communicating an "off" state to the controller, whereas the controller may determine that the reservoir is full responsive to the level switch communicating an "on" state to the controller. In embodiments where the level sensor outputs a signal corresponding to a direct measurement of the level of medical agent within the reservoir, the controller may compare the measurement received from the level sensor to the threshold level to determine if the reservoir is full.

If the reservoir is full (e.g., the level switch is activated or the measured level of medical agent in the reservoir is greater than or equal to the threshold level), the method 1100 proceeds to 1122 and includes unlocking the slide pin to enable slide pin movement from the extended position to a retracted position. This may include, for example, de-energizing the solenoid to adjust the rotating pin to the unlocked position within the slide pin, as indicated at 1124. Alternatively, if the solenoid is already de-energized, the solenoid may remain in the de-energized state. With the rotating pin in the unlocked position, the slide pin is not held in the extended position for engaging and opening the valve of the refill bottle, as described above with respect to 1105. Thus, the slide pin retracts, and medical agent is not transferred from the refill bottle to the reservoir even when the refill bottle is inserted in the fill neck of the reservoir.

At 1126, the method 1100 includes de-activating the medical agent level circuit. Because the reservoir is full, the refill event may be cancelled. Thus, the controller may not continue to monitor the medical agent level for the purpose of the refill event. However, if the medical agent is being consumed, the medical agent level may continue to be monitored by the medical agent circuit (e.g., via a different control method). The method 1100 may then end.

Returning to 1108, if the reservoir is not full (e.g., the level switch is not activated or the measured level of medical agent in the reservoir is less than the threshold level), the method 1100 proceeds to 1110 and includes setting a timer for a threshold duration. The threshold duration may be a pre-determined, non-zero time duration for each refill event over which the refill bottle is expected to be emptied into the reservoir. As one non-limiting example, the threshold duration is 2 minutes, although in other examples, the threshold duration may be longer or shorter than 2 minutes. The timer may be an electronic clock that counts up to the threshold duration from zero or counts down from the threshold duration to zero, for example. In other embodiments, the timer may be a mechanical timer with a mechanical linkage to trip or trigger the rotating pin to disengage the slide pin. In some examples, the slide pin may be used to automatically unlock the slide pin, as will be elaborated below. As another example, the timer may be used as a fallback in case the medical agent level circuit becomes degraded (e.g., a float sticks and does not move with the medical agent level) or loses communication with the controller.

At 1112, the method 1100 includes locking the slide pin in the extended position. This includes energizing the solenoid to adjust the rotating pin to the locked position within the slide pin, as indicated at 1114. As described above with particular reference to FIG. 8A, by energizing the solenoid coil, the solenoid shaft may be further pulled into the solenoid coil, causing the rotating pin to rotate into the locked position. With the rotating pin in the locked position, the slide pin is held in the extended position to engage with and open the refill bottle valve.

At 1116, the method 1100 includes determining if the timer is less than the threshold duration. For example, the timer is considered less than the threshold duration if the clock has not reached the threshold duration from zero (e.g., counting up) or has not reached zero from the threshold duration (e.g., counting down).

If the timer is not less than the threshold duration, then the timer has elapsed (e.g., finished counting up or counting down), and the method proceeds to 1122, as described above. Thus, the solenoid is de-energized to unlock the slide pin from the extended position, enabling the refill bottle to close and move the slide pin to the retracted position. With the refill bottle valve closed, the refill bottle and the reservoir are no longer fluidically coupled, and medical agent no longer flows from the refill bottle to the reservoir. As a result, the refill event is completed.

If the timer is less than the threshold duration (e.g., the timer has not elapsed), the method 1100 proceeds to 1118 and includes determining if the reservoir is full, as described above at 1108. If the reservoir is full, even if the timer has not yet elapsed, the method 1100 proceeds to 1122, as described above.

If the reservoir is not full, the method 1100 proceeds to 1120 and includes maintaining the slide pin locked in the extended position. Thus, the slide pin will continue to hold the refill bottle valve open, thereby enabling fluid communication between the refill bottle and the reservoir, until the reservoir is full or the timer elapses.

Thus, the systems and methods described herein provide for reducing overfilling of a medical device reservoir via medical agent from a refill bottle via an overfill prevention mechanism. As a result, both user exposure to the medical agent and environmental pollution with the medical agent may be reduced. Further, by closing a valve of the refill bottle prior to closing a valve of the medical device reservoir, an amount of the medical agent trapped in a fill assembly of the medical device reservoir may be reduced. As a result, splashing of the medical agent, medical agent loss, user exposure to the medical agent, and environmental accumulation of the medical agent may be further reduced. As some medical agents, such as some anesthetic agents, have ozone-depleting properties, reducing environmental accumulation of the medical agent may reduce ozone depletion. By including a mechanical or electro-mechanical trigger, the overfill prevention mechanism described herein provides a highly flexible system that can be fully automatic or user-controlled. As another example, the user does not have to wait until the device will accept a whole bottle of medical agent before "topping-off" the reservoir between uses and risk agent exposure, as the overfill prevention mechanism manages medical agent transfer between the refill bottle and the reservoir and prevents (or at least reduces) user exposure to the agent even when the refill bottle is not entirely drained and even when the user performs multiple refill bottle insertions. Overall, customer satisfaction may be increased.

A technical effect of including overfill prevention mechanism in a fill assembly of a medical device reservoir is that over filling of the medical device reservoir with a medical agent may be reduced or eliminated, thereby reducing loss of the medical agent to the atmosphere and user exposure to the medical agent at a patient care location.

In an embodiment, a valve shut-off system for a medical device, comprises: first pin movable between a first position where a valve is opened and a second position where the valve is closed, the first pin including a slot; and a second pin having a mating geometry with the slot of the first pin, the second pin adjustable between a locked position that holds the first pin in the first position and an unlocked position that enables movement of the first pin between the first position and the second position.

In examples, the valve shut-off system further comprises an actuator mechanically coupled to the second pin, wherein the actuator adjusts the second pin between the locked position and the unlocked position.

In one example, the actuator includes a float positioned within a reservoir of the medical device, and wherein the actuator adjusts the second pin from the locked position to the unlocked position responsive to the float reaching a threshold level within the reservoir.

In another example, the actuator includes a mechanical timer, and wherein the actuator adjusts the second pin from the locked position to the unlocked position responsive to the mechanical timer elapsing.

In some examples, the actuator includes a solenoid, and wherein the actuator adjusts the second pin from the locked position to the unlocked position responsive to a change in an energization state of the solenoid. As an example, the change in the energization state of the solenoid is responsive to one of a set timer elapsing and a medical agent level in a reservoir reaching a threshold level.

In an example, the slot of the first pin includes a locking geometry that engages with the second pin only when the second pin is in the locked position and a sliding geometry that engages with the second pin only when the second pin is in the unlocked position. In another example, the first pin and the second pin are positioned in a fill assembly of a reservoir of the medical device, and the valve is positioned in a neck of a refill bottle.

In another embodiment, an apparatus for a fill assembly of a medical device reservoir comprises: a fill neck including a central cavity; a first pin positioned at least partially within the central cavity, the first pin movable within the central cavity between a first position and a second position; and a second pin extending though a mating slot in the first pin and rotatable within the mating slot between a first rotated position and a second rotated position.

In an example, the first pin is held in the first position when the second pin is in the first rotated position and is adjustable between the first position and the second position when the second pin is in the second rotated position.

In some examples, the mating slot includes a locking portion, and the second pin includes a mating surface that directly contacts the locking portion when the second pin is in the first rotated position and does not directly contact the locking portion when the second pin is in the second rotated position. As an example, the mating slot further includes a sliding portion extending from the locking portion, the sliding portion narrower than the locking portion, and wherein the mating surface fits within the sliding portion when the second pin is in the second rotated position and does not fit within the sliding portion when the second pin is in the first rotated position.

In one example, the first pin includes a cylindrical body having a central opening extending longitudinally through the cylindrical body, and wherein the mating slot extends transversely through the cylindrical body. In another example, the apparatus further comprises an actuator mechanically coupled to the second pin, the actuator one of a mechanical actuator and an electro-mechanical actuator, and wherein adjusting a position of the actuator rotates the second pin between the first rotated position and the second rotated position.

In still other examples, the apparatus further comprises a reservoir valve extending between an interior of the medical device reservoir and the central cavity, wherein a neck of a refill bottle opens the reservoir valve when the neck of the refill bottle is inserted into the fill neck by at least a first distance; and an overfill ring encircled by the fill neck and extending between the fill neck and the interior of the medical device reservoir, wherein the second pin is at least partially housed within the overfill ring. As an example, the first pin opens a refill bottle valve of the refill bottle only when the first pin is in the first position and the neck of the refill bottle is inserted into the fill neck by at least a second distance, greater than the first distance, and wherein fluid drains from the central cavity into the medical device reservoir after the refill bottle valve closes.

In still another embodiment, a method for refilling a reservoir of a medical device comprises: opening a first valve positioned within a fill assembly of the reservoir by engaging the first valve with a neck of a refill bottle; after opening the first valve, opening a second valve positioned within the neck of the refill bottle by locking a position of a slide pin in the fill assembly via a rotating pin; and flowing medical agent from the refill bottle to the reservoir via the open first valve and the open second valve.

In examples, the method further comprises closing the second valve positioned within the neck of the refill bottle by unlocking the position of the slide pin in the fill assembly via the rotating pin; and after closing the second valve, closing the first valve by disengaging the first valve with the neck of the refill bottle. In an example, locking the position of the slide pin in the fill assembly via the rotating pin includes adjusting the rotating pin to a first rotated position that engages a mating surface of the rotating pin with a locking slot of the slide pin, and unlocking the position of the slide pin the fill assembly via the rotating pin includes adjusting the rotating pin to a second rotated position that does not engage the mating surface of the rotating pin with the locking slot of the slide pin. As one example, adjusting the rotating pin to the first rotated position is responsive to an initiation of a refill event, and adjusting the rotating pin to the second rotated position is responsive to an indication that the refill event is completed.

FIGS. 3A-9B show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another and/or relative to provided reference axes. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another and with respect to gravity. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

I claim:

1. A valve shut-off system for a medical device, comprising:
    a first pin movable between a first position where a valve is opened and a second position where the valve is closed, the first pin including a slot; and
    a second pin having a mating geometry with the slot of the first pin, the second pin adjustable between a locked position that holds the first pin in the first position and an unlocked position that enables movement of the first pin between the first position and the second position.

2. The valve shut-off system of claim 1, further comprising an actuator mechanically coupled to the second pin, wherein the actuator adjusts the second pin between the locked position and the unlocked position.

3. The valve shut-off system of claim 2, wherein the actuator includes a float positioned within a reservoir of the medical device, and wherein the actuator adjusts the second pin from the locked position to the unlocked position responsive to the float reaching a threshold level within the reservoir.

4. The valve shut-off system of claim 2, wherein the actuator includes a mechanical timer, and wherein the actuator adjusts the second pin from the locked position to the unlocked position responsive to the mechanical timer elapsing.

5. The valve shut-off system of claim 2, wherein the actuator includes a solenoid, and wherein the actuator adjusts the second pin from the locked position to the unlocked position responsive to a change in an energization state of the solenoid.

6. The valve shut-off system of claim 5, wherein the change in the energization state of the solenoid is responsive to one of a set timer elapsing and a medical agent level in a reservoir reaching a threshold level.

7. The valve shut-off system of claim 1, wherein the slot of the first pin includes a locking geometry that engages with the second pin only when the second pin is in the locked position and a sliding geometry that engages with the second pin only when the second pin is in the unlocked position.

8. The valve shut-off system of claim 1, wherein the first pin and the second pin are positioned in a fill assembly of a reservoir of the medical device, and the valve is positioned in a neck of a refill bottle.

* * * * *